(12) United States Patent
Chapman

(10) Patent No.: US 7,481,578 B2
(45) Date of Patent: Jan. 27, 2009

(54) DIGITAL RADIOGRAPHY APPARATUS

(75) Inventor: Raymond P. Chapman, Fairport, NY (US)

(73) Assignee: Cartstream Health, Inc., Rochester, NY (US)

(*) Notice: Subject to any disclaimer, the term of this patent is extended or adjusted under 35 U.S.C. 154(b) by 0 days.

(21) Appl. No.: 11/532,573

(22) Filed: Sep. 18, 2006

(65) Prior Publication Data
US 2008/0069308 A1 Mar. 20, 2008

(51) Int. Cl.
H05G 1/02 (2006.01)
(52) U.S. Cl. ............... 378/197; 378/196; 378/204
(58) Field of Classification Search ......... 378/193–198, 378/204, 205
See application file for complete search history.

(56) References Cited

U.S. PATENT DOCUMENTS

| 3,254,223 | A | 5/1966 | Koerner et al. |
|---|---|---|---|
| 3,702,935 | A | 11/1972 | Carey et al. |
| 4,426,725 | A | 1/1984 | Grady |
| 4,501,011 | A | 2/1985 | Hauck et al. |
| 4,845,495 | A | 7/1989 | Bollard et al. |
| 5,018,178 | A * | 5/1991 | Katsumata ............... 378/91 |
| 6,234,672 | B1 | 5/2001 | Tomasetti et al. |
| 6,325,537 | B1 | 12/2001 | Watanabe |
| 6,428,206 | B1 * | 8/2002 | Watanabe ............... 378/197 |
| 2006/0078091 | A1 | 4/2006 | Lasiuk et al. |
| 2008/0069304 | A1 * | 3/2008 | Muszak et al. ............ 378/114 |

FOREIGN PATENT DOCUMENTS

EP 1 698 280 A2 9/2006

* cited by examiner

Primary Examiner—Jurie Yun

(57) ABSTRACT

A radiography apparatus having an x-ray source, an x-ray imaging detector, and a support structure. The support structure is coupled to the x-ray source and to the x-ray detector and rotatable about two orthogonal axes and linearly moveable. The x-ray source and the x-ray imaging detector are each independently rotatable about third and fourth axes, respectively. The apparatus provides an operator with a number of degrees of freedom of motion of the x-ray source and the x-ray imaging detector to move them to different positions relative to a subject.

4 Claims, 23 Drawing Sheets

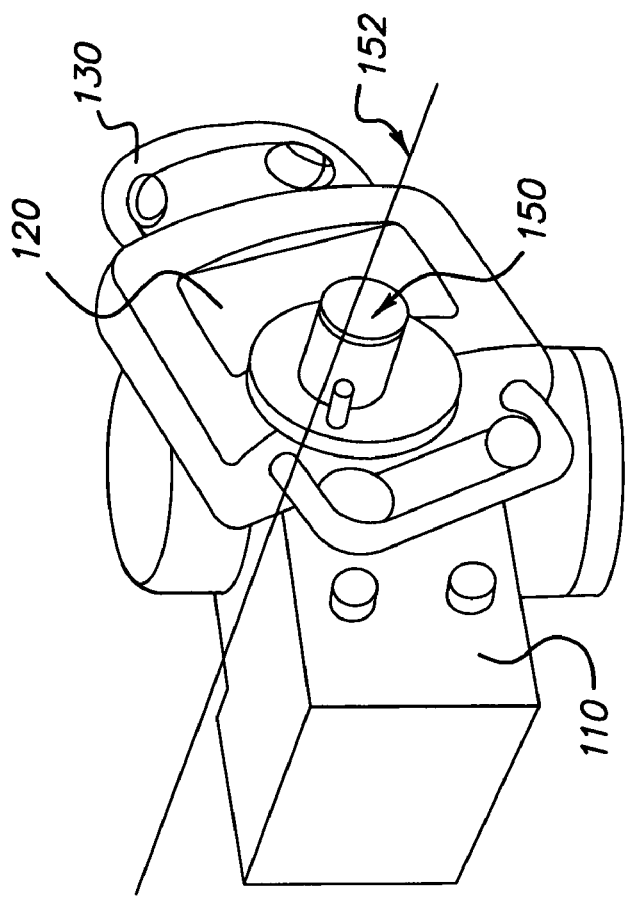
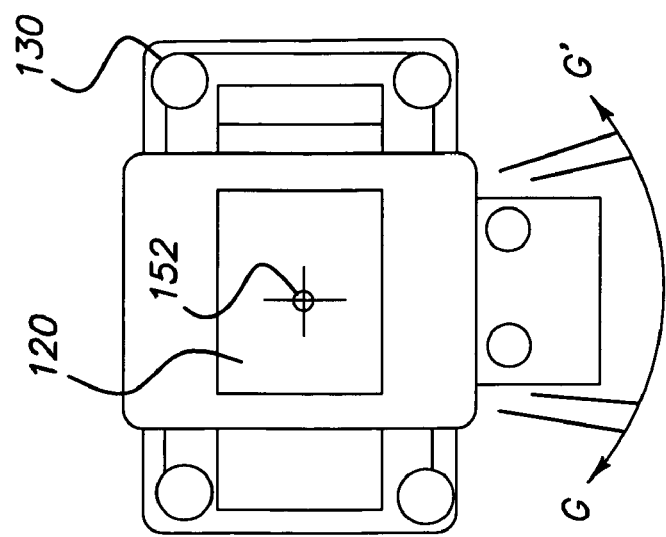
FIG. 3B
FIG. 3A

DIGITAL RADIOGRAPHY APPARATUS

RELATED APPLICATIONS

Reference is made to commonly assigned application entitled "Digital Radiography Imaging System with Rotatable Display and Controls", U.S. Ser. No. 11/522,868, filed on even date, in the names of Muszak et al., incorporated herein by reference.

Reference is made to commonly assigned patent application entitled "Radiography Apparatus with Multiple Work Zones", U.S. Ser. No. 11/522,863, filed on even date, in the name of Muszak et al., incorporated herein by reference.

FIELD OF THE INVENTION

This invention generally relates to digital radiography and more particularly relates to a digital radiography imaging apparatus.

BACKGROUND OF THE INVENTION

Digital Radiography (DR) systems are employed in the field of medical technology for capturing digital medical images. Some digital radiography imaging systems have an X-ray source and an X-ray imaging detector that are coupled together and supported in a manner that provides for a plurality of degrees of freedom of movement so that the imaging system can be properly positioned relative to a subject. See for example, U.S. Pat. No. 4,501,011 (Hauck) and U.S. Pat. No. 4,426,725 (Grady).

Often, an operator control interface having a display screen is integrated into the system. Some digital radiography imaging systems will "flip" and redraw the image on the display screen after the display and X-ray source have been subject to a given amount of angular rotation (e.g., a 45 degree angle in either direction) by an operator in positioning the source. In other digital radiography imaging systems, such as shown in U.S. Pat. No. 3,702,935 (Carey), the display screen is mounted on an independent support arm that does not move in conjunction with the movement of X-ray source. Rather, it maintains a fixed position. Such systems have limited ability to handle different orientations of individuals for imaging, and must include additional support structure for the display monitor. Furthermore, such systems occupy significant floor space, which is disadvantageous in emergency room situations.

An issue relating to existing radiography systems is operator ergonomics. Even when systems allow flexibility for positioning X-ray source and detector components, operator access to controls and to system information can be hampered by the positioning of support structures and the need for making adjustments to suit individual patients.

There exists a need for a digital radiography system having an X-ray source and an X-ray imaging detector that are coupled together and supported to provide for a plurality of degrees of freedom of movement so that the imaging system can be properly positioned relative to a subject. Such a system can allow expanded operator work zone configurations so that the imaging apparatus can be set up from a number of operator positions, and/or alleviates the need for constant operator movement between the patient and the operator control console.

SUMMARY OF THE INVENTION

An object of the present invention to provide a radiography apparatus having an x-ray source, an x-ray imaging detector, and a support structure coupling the source and the x-ray detector and rotatable about a predetermined axis for positioning about a subject.

Accordingly to one aspect of the present invention, there is provided a radiography apparatus, comprising: an x-ray source; an x-ray imaging detector; and a support structure. The support structure is coupled to the x-ray source and to the x-ray detector. The support structure includes a translational assembly and a rotational assembly. The translational assembly provides simultaneous linear movement of the x-ray source and to the x-ray detector in opposing directions. The rotational assembly provides rotation of the x-ray source and the x-ray detector about two orthogonal axes.

The present invention provides a digital radiography imaging apparatus capable of responding to operator instructions that are entered at one of a number of different operator locations.

The present invention provides a compact, adjustable digital radiography imaging system where the X-ray source and X-ray imaging detector are coupled. Typical imaging systems are generally much larger, or have separate pieces of equipment that work together; such systems are mechanically complex, and have disadvantages in usability, cost and reliability.

The adjustability of the present invention allows an operator to position the X-ray source and X-ray imaging detector to achieve suitable positioning to accommodate subjects for imaging (including ambulatory and non-ambulatory patients standing, reclining or in seated position).

BRIEF DESCRIPTION OF THE DRAWINGS

The foregoing and other objects, features, and advantages of the invention will be apparent from the following more particular description of the embodiments of the invention, as illustrated in the accompanying drawings.

FIGS. 3A and 3B show the coupling between the X-ray source and operator controls of the digital radiography system of FIG. 1.

DETAILED DESCRIPTION OF THE INVENTION

Figure 1:
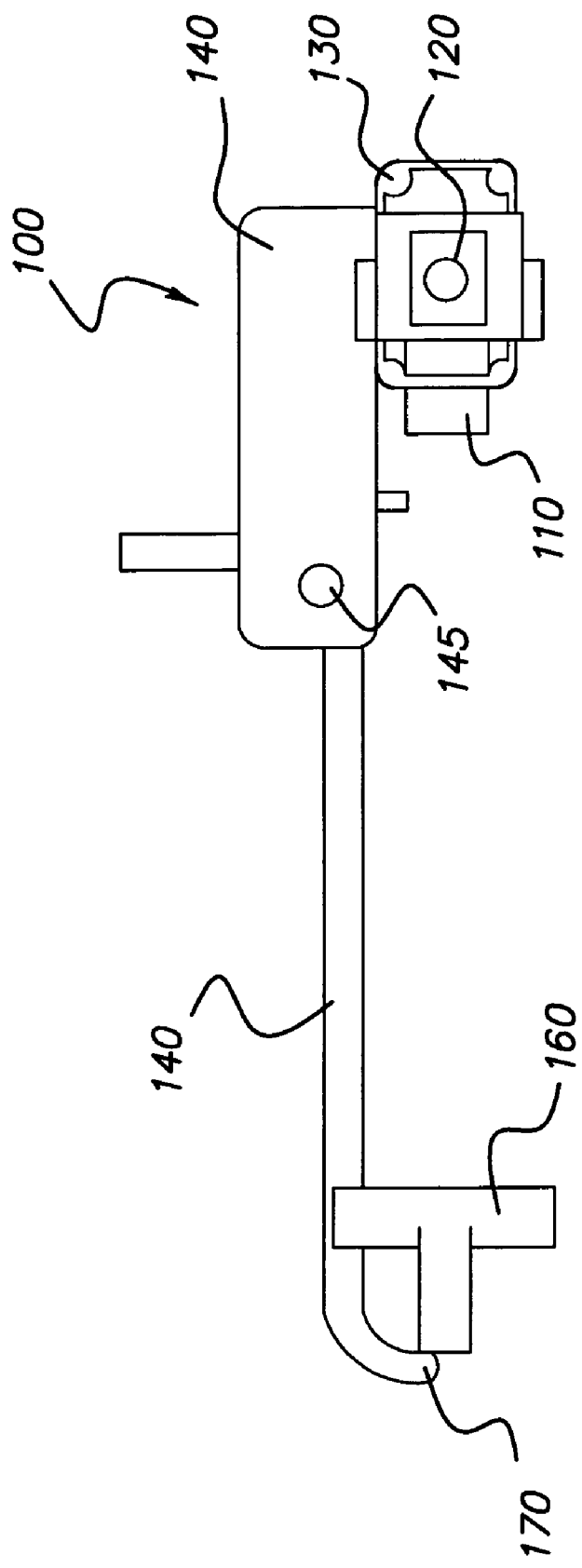
FIG. 1 shows a digital radiography system in accordance with the present invention.

The following is a detailed description of the preferred embodiments of the invention, reference being made to the drawings in which the same reference numerals identify the same elements of structure in each of the several figures.

The present invention is directed to a digital radiography system wherein an X-ray or other suitable radiation source projects radiation through a subject (e.g., patient) to produce an image captured by an imaging detector. The radiation source and imaging detector can be positioned in various orientations to capture an image of a patient. The present invention provides multiple redundant work zones, each work zone including appropriate setup controls and a display for setup and operation of the digital radiography system. The description that follows describes an embodiment using X-ray imaging; however, it is noted that the apparatus and method of the present invention can be more applied for other suitable types of diagnostic imaging.

Referring to FIG. 1, a digital radiography system 100 has an X-ray source 110, a first display 120, an operator control interface 130, a support structure 140, and an X-ray imaging detector 160 with a coupling 170. X-ray source 110 is connected to a support structure 140 by a coupling 112 (see FIGS. 6-7) that allows X-ray source 110 to rotate in the C and C' directions (shown in FIG. 4). Coupling 170 permits X-ray imaging detector 160 to move in the D and D' directions (illustrated in FIG. 4), and to rotate so as to orient X-ray imaging detector 160 into a portrait or landscape position.

Figure 4:
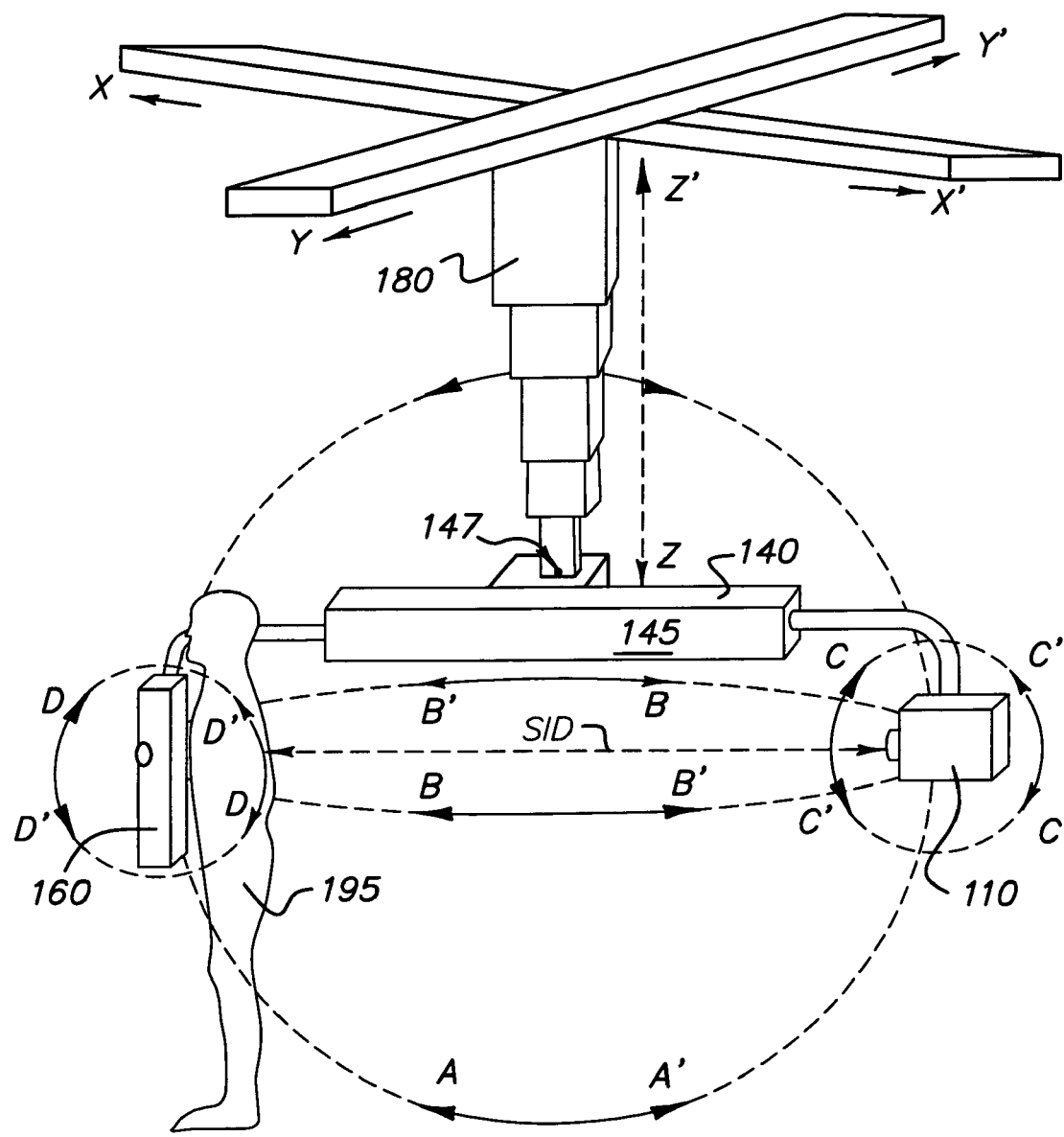
FIG. 4 shows a diagrammatic view of the digital radiography system of FIG. 1 (and labeled axes X, Y, Z, A, B, C and D) with a subject to be imaged in a standing position.

Support structure 140 is pivotally mounted for rotation about an axis 145 as illustrated in FIG. 4.

Figure 5:
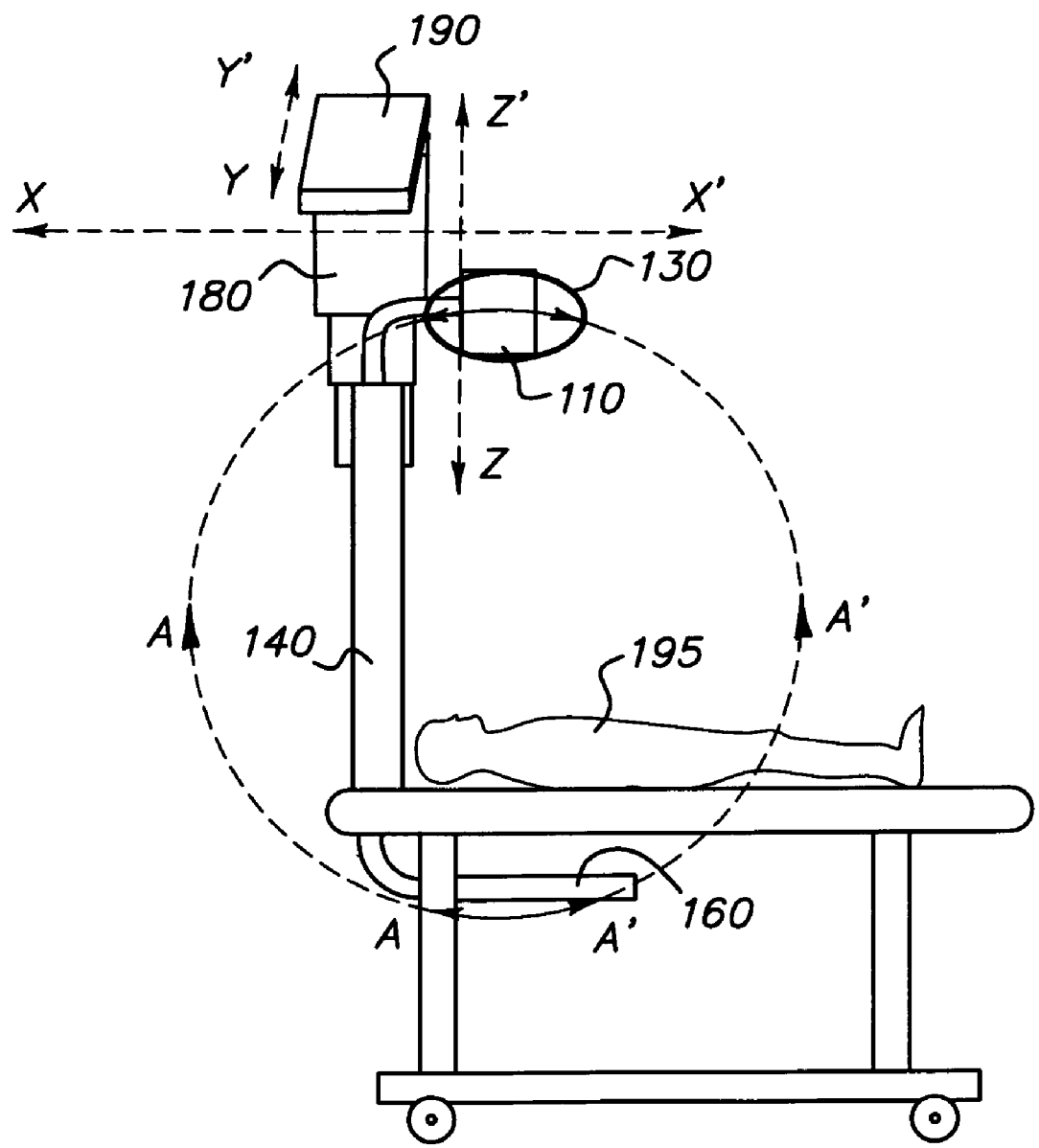
FIG. 5 shows a diagrammatic view of the digital radiography system of FIG. 1 with a subject to be imaged in a reclined position.
Figure 6:
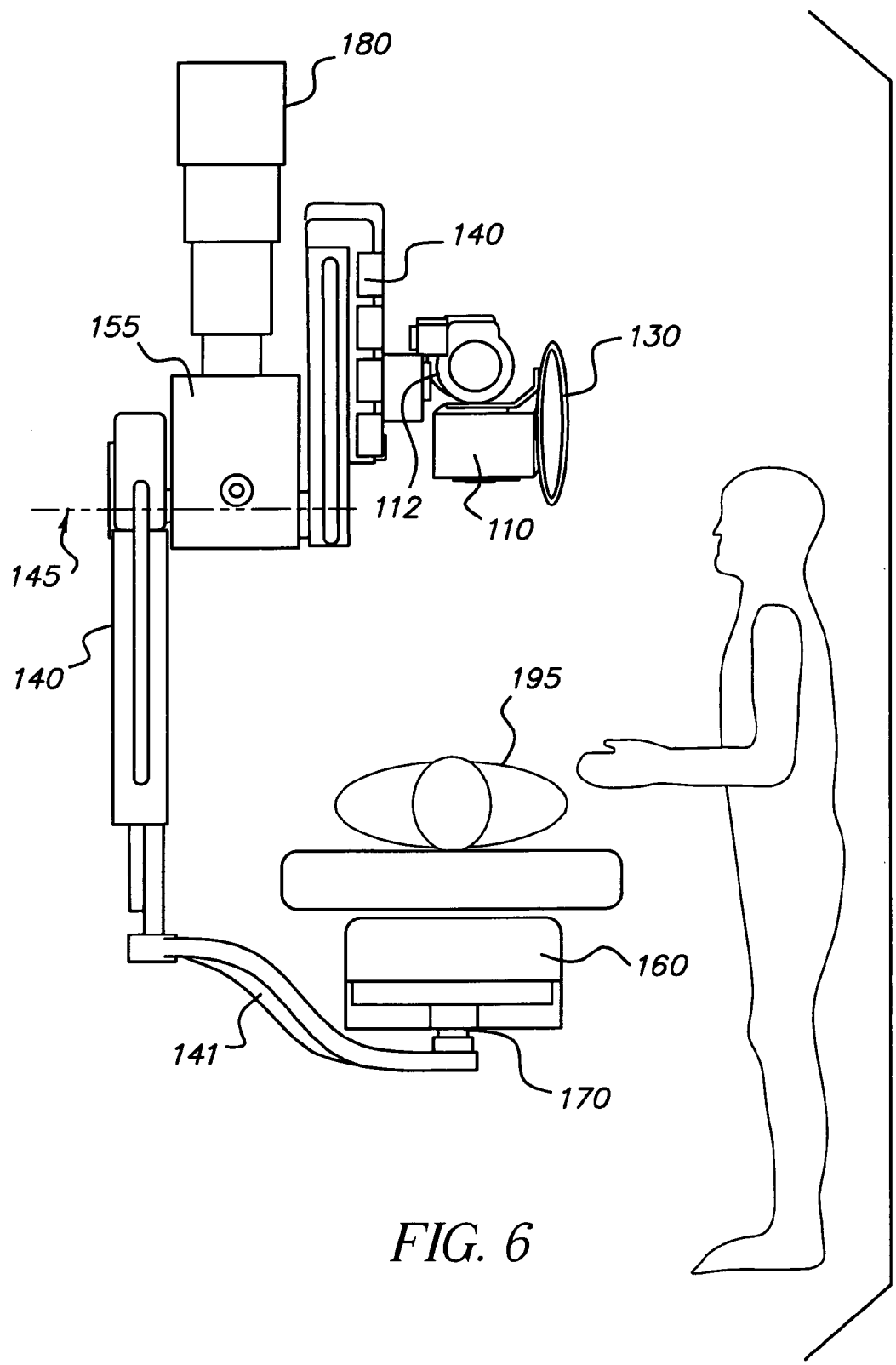
FIG. 6 shows another diagrammatic view of the digital radiography system of FIG. 1 with a subject to be imaged in a reclined position.

Support structure 140 is linearly adjustable (e.g., in the E and E' directions shown in FIG. 7) so as to allow an operator to set the source-to-image (SID) distance between X-ray source 110 and X-ray imaging detector 160. X-ray source 110 is linearly moveable in directions F and F' (shown in FIG. 7) along support structure 140 so as to adjust the source-to-image distance before capturing an image of a subject as shown in FIGS. 4-6. Support structure 140 is further rotatable about an axis 145 in the A and A' directions illustrated in FIG. 4 by an operator in preparation for capturing an image of subject 195.

Operator control interface 130 and first display 120 are mounted for movement about an axis 152 in the G and G' directions (see FIG. 3). Axis 152 is substantially parallel to axis 145. As used herein, the phrase "substantially parallel" is intended to mean that axis 145 and axis 152 are close enough to parallel so as to maintain the information presented on first display 120 close enough to the same orientation relative to an operator so that the position of the operator does not have to change when the positions of the X-ray source and the X-ray imaging detector are changed, regardless of the direction and extent that support structure 140 is rotated. Operator control interface 130 has grip points incorporated into its handle to maximize grasp by an operator. These grip points can be optimized to allow for left-handed or right-handed use.

As illustrated in FIGS. 4-6, support structure 140 is connected to telescoping support member 180 by a coupling 155 (see FIG. 6). The telescoping support member is designed to be suspended from a ceiling of a room by a moveable base 190 (illustrated in FIG. 5). Moveable base 190 can be attached to a typical ceiling-mounted X-Y rail structure using a carriage system with a plurality of wheels or other suitable movement system. Thus, with such an X-Y rail structure, moveable base 190 is selectably moveable in the X, X', Y and Y' directions illustrated in FIGS. 4 and 5. Moveable base 190 or coupling 155 can include a rotational mechanism, which is used in rotating telescoping support member 180 or support structure 140 about an axis 147 in the B and B' directions illustrated in FIG. 4.

Telescoping support member 180 is adjustable in the Z and Z' directions shown in FIGS. 4 and 5 to varying positions between a collapsed position and an extended position. That is, telescoping support member 180 is configured to slide inward and outward in overlapping sections. In a collapsed position, telescoping support member 180 is moved in the Z' direction and disposed towards moveable base 190 close to the ceiling. In an extended position, telescoping support member 180 is moved in the Z direction and is disposed away from moveable base 190 close to the floor. Telescoping support member 180 can move in Z and Z' directions to discrete positions intermediate of the collapsed and extended positions. This motion allows for the imaging of objects of various heights and orientations between the collapsed and extended positions.

Support structure 140 allows digital radiography system 100 to image a variety of subjects (e.g., subject 195 illustrated in FIGS. 4-6), which can be an individual or a body part of the individual), whether the subject is standing (e.g., see subject 195 of FIG. 4), reclining on a table (e.g., see subject 195 of FIGS. 5 and 6), or sitting. Support structure 140 is configured to slide inward and outward in overlapping sections in directions E and E' (shown in FIG. 7), so as to move the location of X-ray imaging detector 160. X-ray source 110 is moveable linearly to discreet positions in the F and F' directions (illustrated in FIG. 7) along support structure 140 to provide further adjustment of digital radiography system 100 for imaging. The positioning of X-ray source 110 and X-ray imaging detector 160 by an operator can achieve an appropriate source-to-image distance for imaging of the subject to occur. As indicated in FIG. 4, the source-to-image distance is the linear distance between X-ray source 110 and X-ray imaging detector 160.

Figure 8:
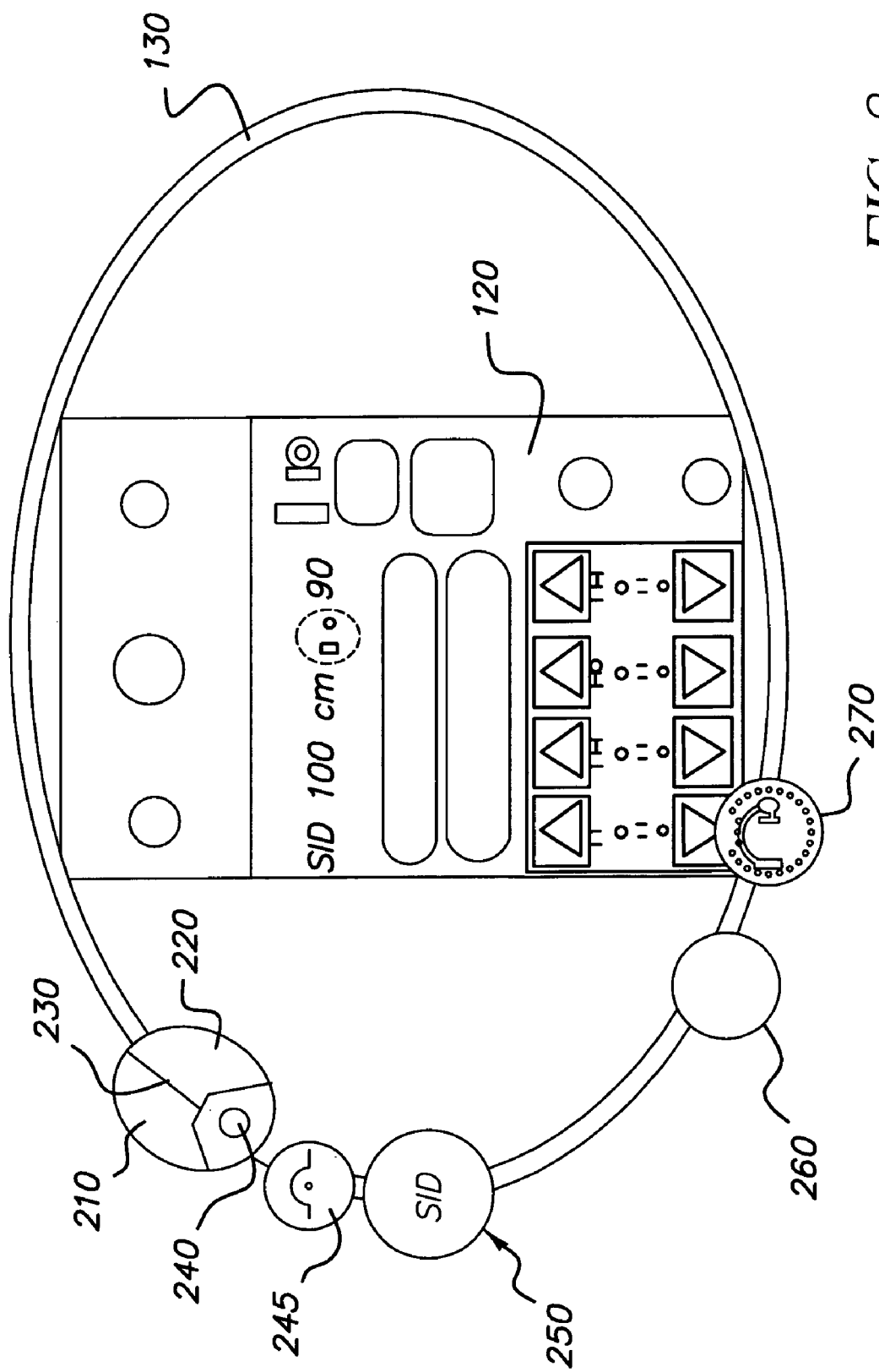
FIG. 8 shows a diagrammatic view of a display and operator control interface for a digital radiography system of FIG. 1.

FIG. 8 illustrates an exemplary display screen for first display 120 and control setup for operator control interface 130. As shown, operator control interface 130 has X-direction control 210, Y-direction control 220, Z-direction control 230, B-direction control 240, detent skip control 245, source-to-image distance release control 250, X-ray source tilt control 260, A-direction control 270, X-ray imaging detector release control (not shown), or any suitable combination thereof.

X-direction control 210 permits moveable base 190 to move in the X and X' directions (see FIG. 4). Similarly, Y-direction control 220 permits control the movement of moveable base 190 in the Y and Y' directions (see FIG. 4), and Z-direction control 230 permits adjustment of telescoping support member 180 in the Z and Z' directions. In other words, controls 210, 220, and 230 allow an operator to control the forward, back, left, right, up, or down movements of support structure 140. As described above, movement of base 190 in the X, X', Y, and Y' directions can be achieved through use of the rails on the ceiling, and movement in the Z and Z' directions is permitted by the sliding inward and outward of the overlapping sections of telescoping support member 180. B-direction control 240 allows an operator or technician to control the rotational motion of support structure 140 in a plane parallel to the ground (e.g., movement in the B and B' directions illustrated in FIG. 4 as illustrated in FIGS. 2 and 4).

Detent skip control 245 allows an operator to bypass detents (e.g., detents fixed by manufacturing or detents added through software configuration) that represent predefined amounts of movement of a structure about an axis or in a particular direction. Movement from detent to detent in a particular direction represents a predefined amount of movement in a direction or about an axis. The detents can be set by operators at particular locations that are expected to be common stoppage points of motion along an axis or direction. The detents permit the operator to reach these predefined points without overshooting, or the need of additional fine positioning adjustments. For example, detents can be used to define discrete amounts of movement for support structure 140 in the A, A', B, and B' directions illustrated in FIG. 4. Detents can also be used to define discrete amounts of movement of moveable base 190 in the X, X', Y, and Y' directions (see FIGS. 4 and 5). In another example, detents can be predefined for movement of X-ray source 110 in the C and C' directions, or detents can be predefined for X-ray imaging detector 160 in the D and D' directions. The detent will normally stop the motion of the structure at the detent point along a given direction or about an axis. By using detent skip control 245, the operator can move the device or structure without interruption.

Figure 2:
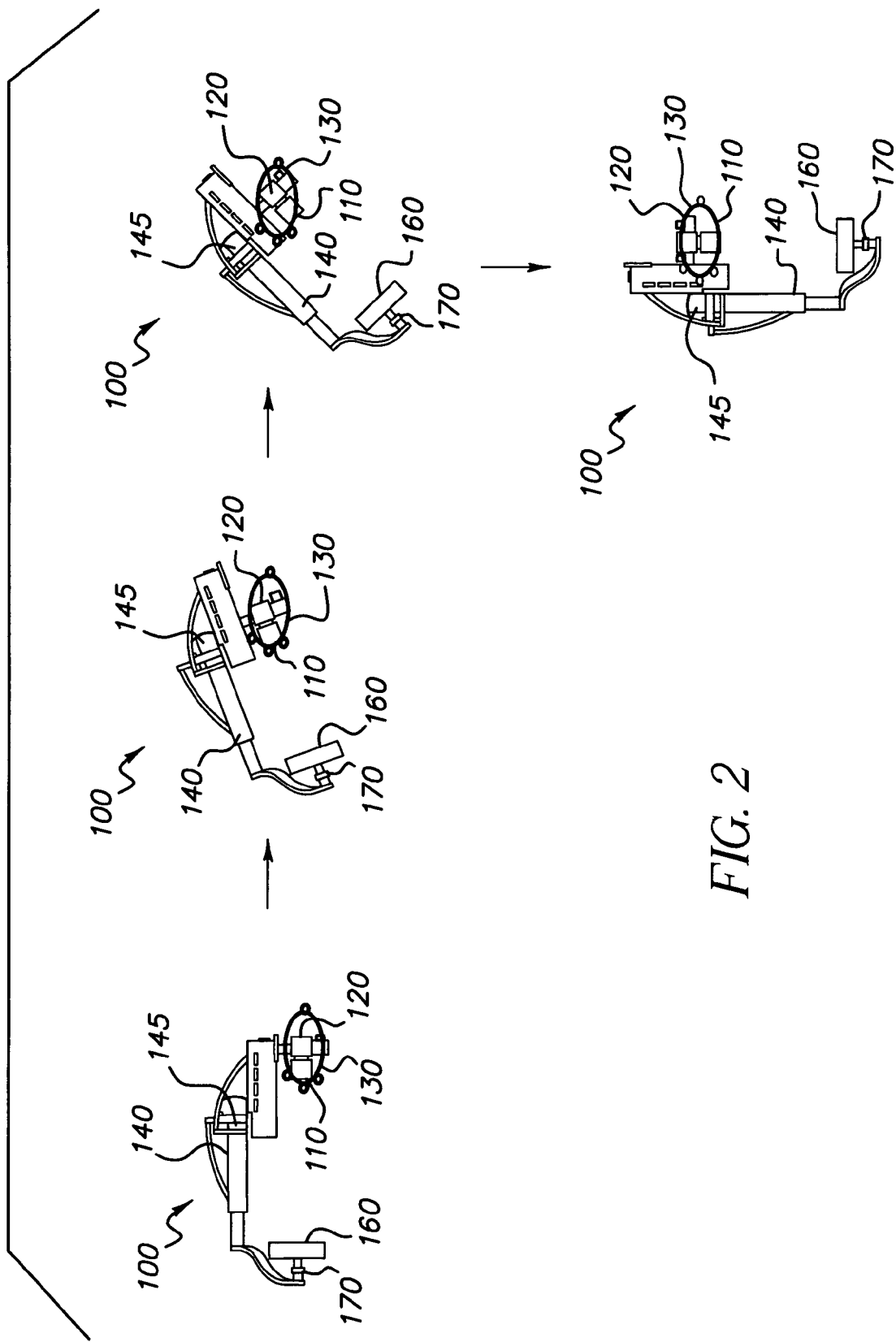
FIG. 2 is a series of views of the digital radiography system of FIG. 1 in various positions in accordance with present invention.

A-direction control 270 allows an operator or technician to rotate direct radiography system 100 in a plane perpendicular to the ground (e.g., movement about the A-axis as shown in FIG. 2). Source-to-image distance release control 250 can control movement of support structure 140 (for movement of X-ray imaging detector 160 in the E and E' directions indicated in FIG. 7). Using source-to-image distance release control 250, an operator can also move X-ray source 110 in the F and F' directions indicated in FIG. 7 on support structure 140 so as to change the source-to-image distance (as illustrated in FIG. 4) between X-ray source 110 and X-ray imaging detector 160. X-ray source tilt control 260 allows an operator or technician to adjust the angular movement of X-ray source 110 in the C and C' directions (as illustrated in FIG. 4).

Turning again to FIG. 7, digital radiography system 100 includes a second display 280 and second controls 290. Second display 280 is coupled to support structure 140 to provide an alternative display to an operator of the same information provided on first display 120. Second display 280 is fixed in a position on support structure 140 (in contrast to first display 120, where coupling 150 allows rotational movement of first display 120 and operator control interface 130 so as to maintain a consistent position relative to an operator). Second controls 290 or third controls 292 can provide duplicate controls for X-direction control 210, Y-direction control 220, Z-direction control 230, B-direction control 240, detent skip control 245, SID release control 250, X-ray source tilt control 260, A-direction control 270, D-direction control, or any suitable combination thereof (in addition to these controls being located on operator control interface 130 or on first display 120). These controls can have any suitable arrangement. These additional controls are advantageous, for example, if an operator or technician is located adjacent to second controls 290 or third controls 292, and needs to further adjust the operation and positioning of X-ray source 110 and X-ray imaging detector 160 of digital radiography system 100.

The term "control console" as used herein has a conventional meaning as applied to an apparatus or system. A control console operates as a control panel, and can include one or more operator controls and some form of display.

Redundant displays have been used in fields other than medical imaging, such as avionics applications. For example, in U.S. Pat. No. 4,845,495 (Bollard et al.) entitled "Integrated Avionics Control and Display Arrangement", redundant display enables a pilot to view critical instrumentation data from a number of different head positions. Redundancy has also been used in robotic and industrial applications for controlling remote X-ray inspection of pipelines, described in U.S. Patent Application Publication No. 2006/0078091 (Lasiuk et al.) entitled "Delivering X-Ray Systems to Pipe Installations". In the Lasiuk et al. disclosure, control redundancy enables both local and remote control of a mobile scanning apparatus with an x-ray source and sensor mounted on an aerial boom that is used for radiographic industrial pipeline imaging. However, control redundancy principles have not been put to use in medical imaging applications.

The present invention employs principles of redundant display and controls with digital radiography apparatus, based on considerations of operator ergonomics and efficiency and improved service and support for the patient.

With the present invention, multiple redundant work zones enable an operator to control the initial setup of a digital radiography apparatus when working from any of two or more different positions. The use of multiple work zones provides feedback on setup characteristics so that adjustments can be made, and results observed, with the operator situated at a convenient location. The arrangement of the present invention allows the radiologist or technician to work from a position that is suited for efficiently setting up to obtain x-ray images from the patient and reduce the need for medical personnel to be moving back and forth between a control console and the patient. It further provides flexibility in operation, providing an opportunity to display different image content from different work zones, such as to display instructions to the patient or to display a selected set of images for maintaining patient attention during the imaging process. Increased flexibility is also available for operator control functions, allowing all or some portion of the operator command set to be available from any work zone. Thus, in addition to allowing functional redundancy where desirable, the method and apparatus of the present invention can also control the function of each work zone independently of the others, providing only those functions needed/desired from any working position. Display and control hardware can be selectively enabled or disabled or have its function changed by the operator to serve the needs of the patient and to improve the efficiency of the radiological imaging facility.

The present invention is directed to improving the usability of digital radiography system 100 by creating two or more separate work zones for setup of the system. Each work zone is supported by an operator console that provides the operator interface tools for controlling system setup.

Figure 9:
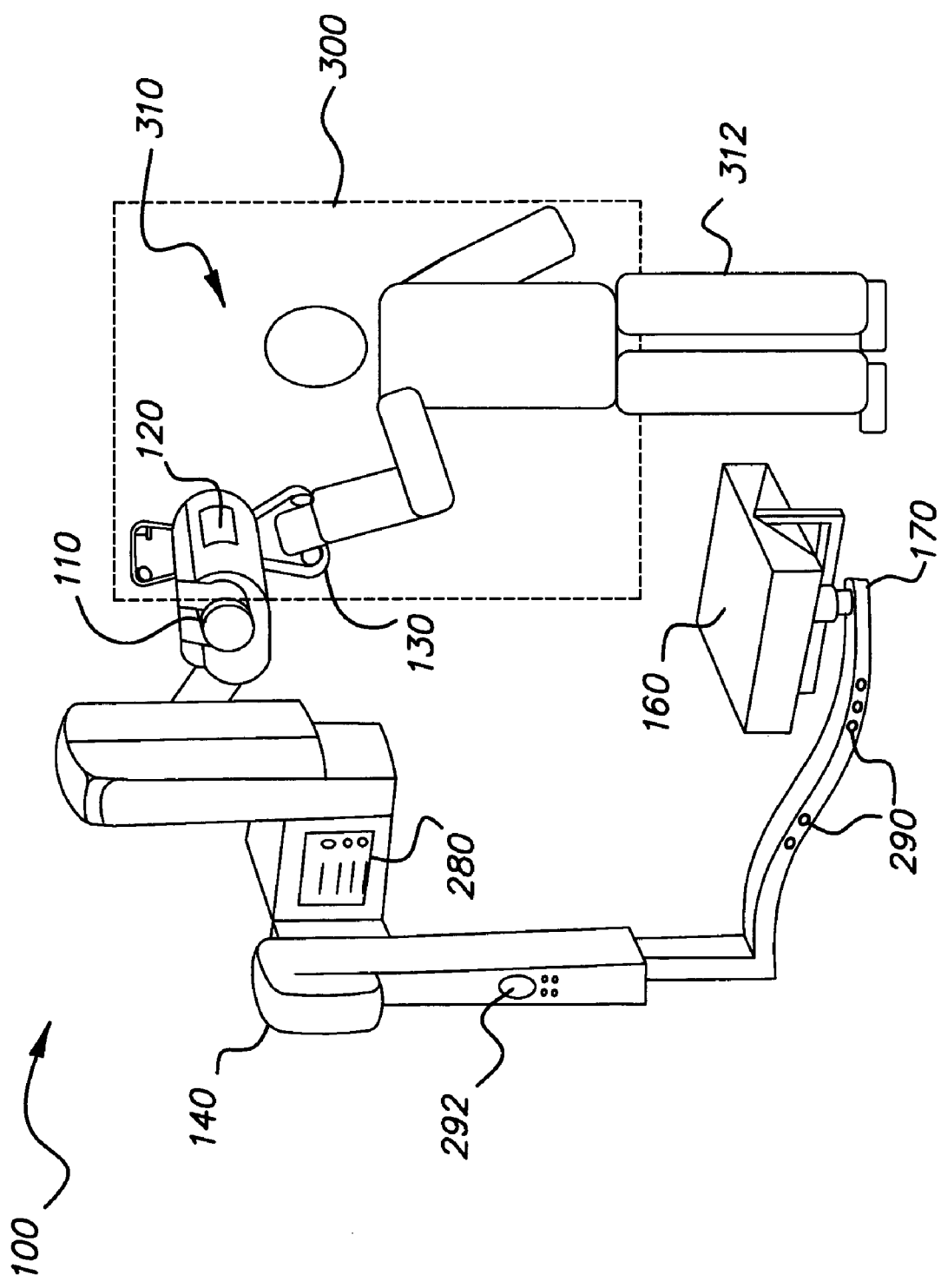
FIG. 9 shows a perspective view showing the position of a first work zone relative to the digital radiography system according to one embodiment.

Referring to FIG. 9, there is shown an embodiment of digital radiography system 100 showing a first work zone 300, shown in dotted outline, that is situated in a conventional area typically used for equipment operation. Work zone 300 employs an operator console 310 having first display 120 and first operator control interface 130 as an instruction entry or command entry device, as previously described.

Figure 13:
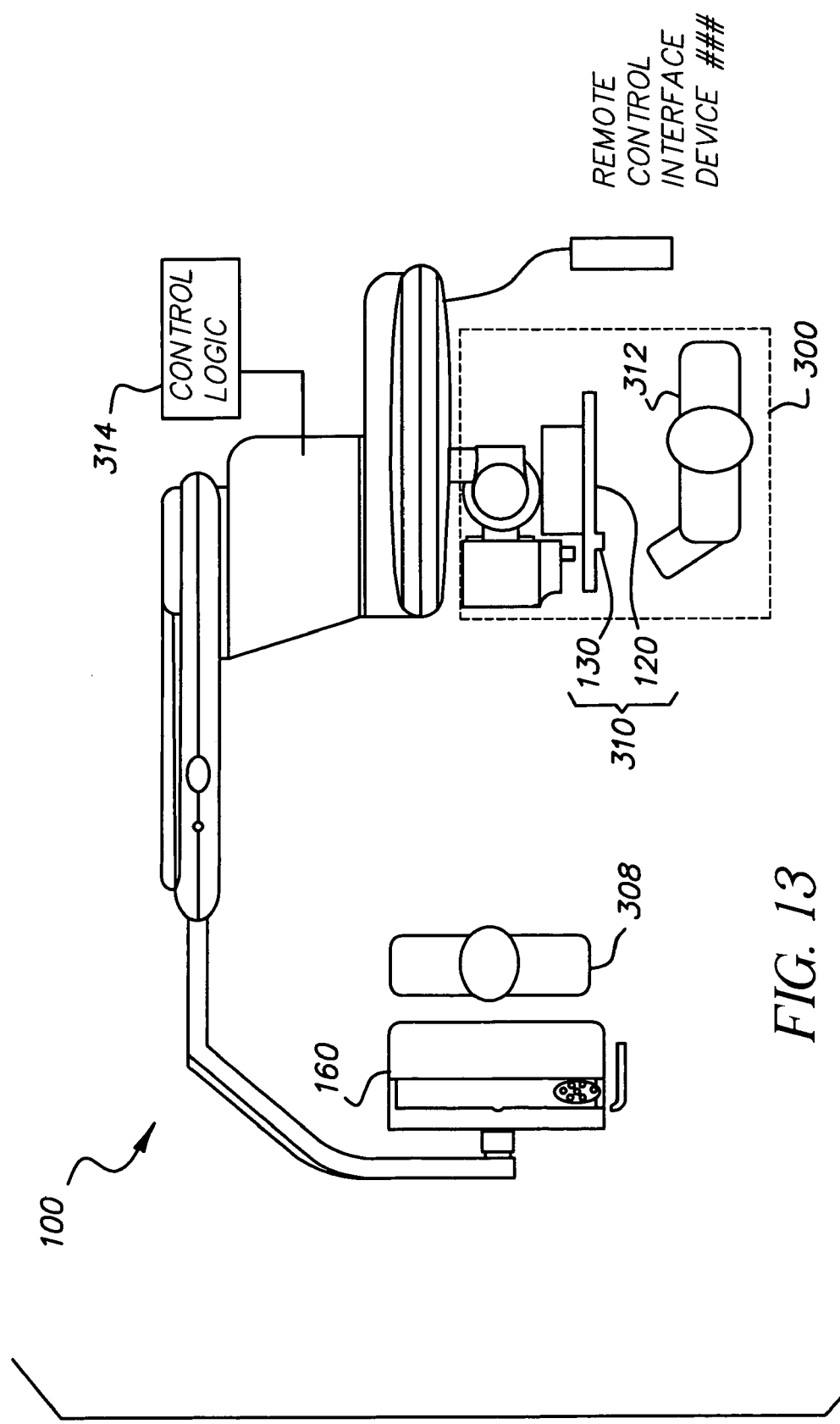
FIG. 13 shows a top view showing the position of a first work zone.

Work zone 300 is typically the primary work area for the operator in one embodiment. This work zone is useful when X-ray imaging detector 160 is generally oriented in the horizontal position, for positioning beneath the patient as shown in FIG. 9, or may be used with imaging detector 160 oriented vertically (as shown in FIG. 13).

Figure 10:
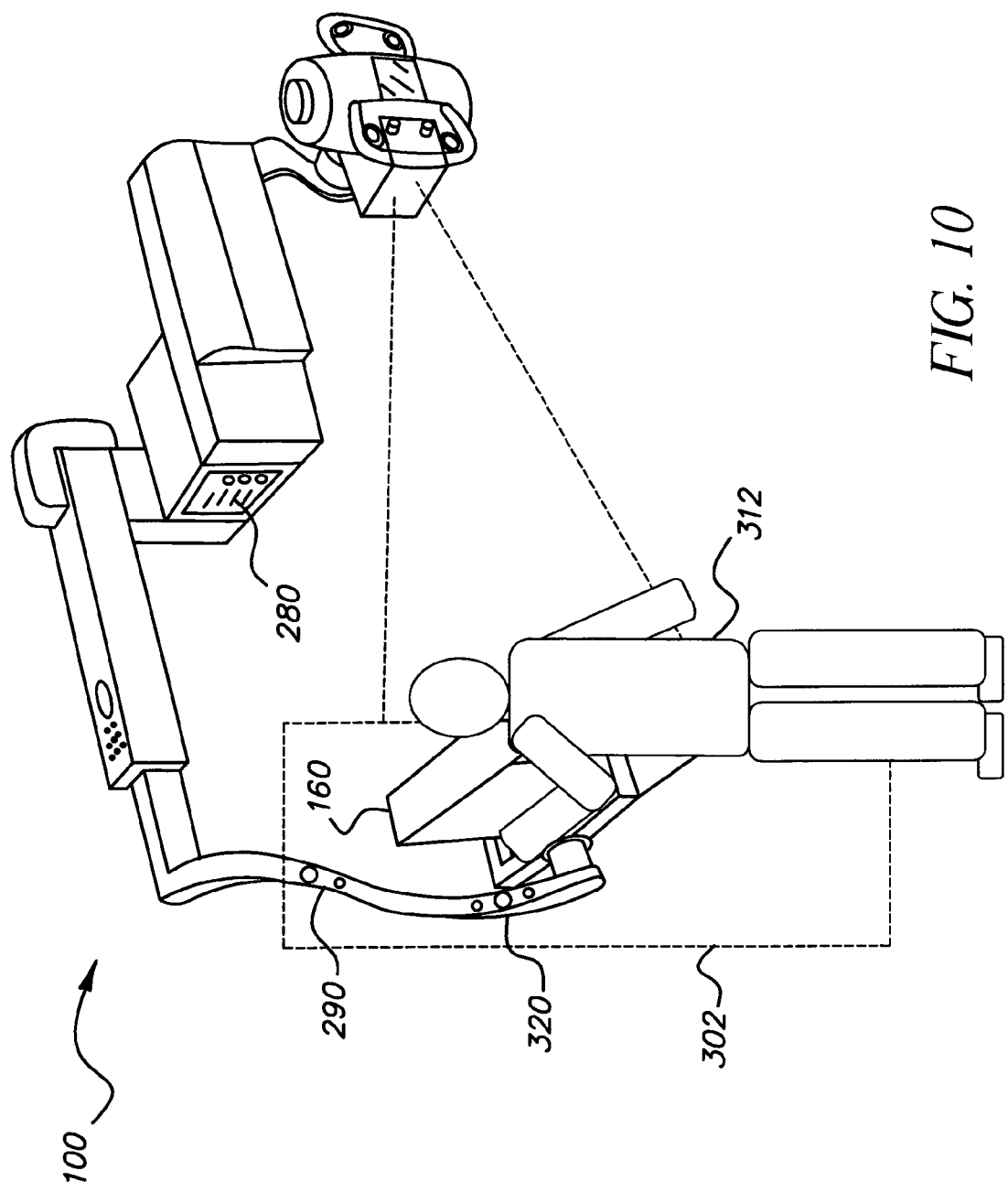
FIG. 10 shows a perspective view showing the position of a second work zone relative to the digital radiography system according to another embodiment.

FIG. 10 shows a second work zone 302, shown in dotted line, that is also available using the present invention. Second work zone 302 can be useful when X-ray imaging detector 160 is generally oriented in the vertical position. Work zone 302 uses a separate operator console 320 having a second display 280 and a second control 290.

Figure 11:
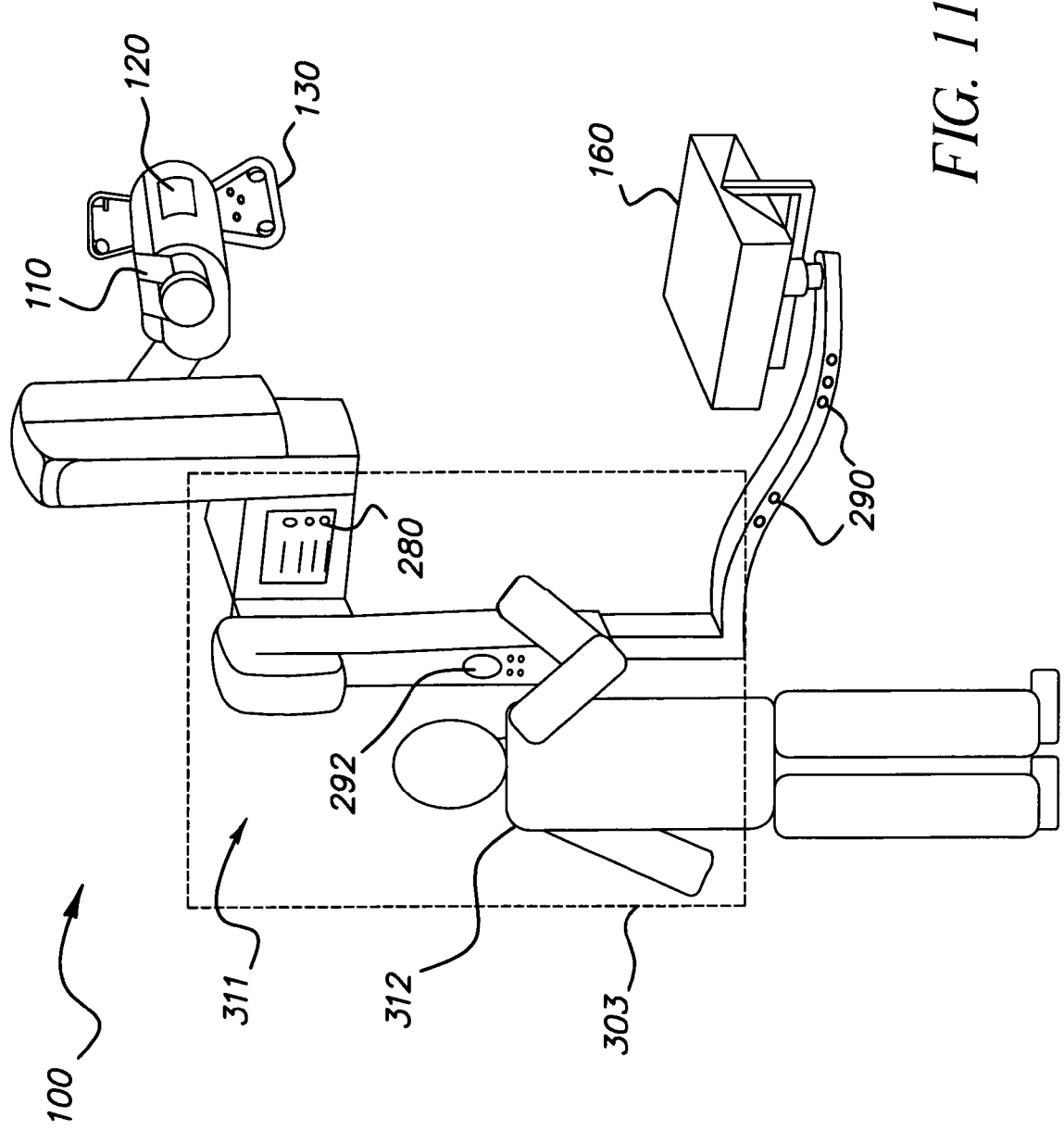
FIG. 11 shows a perspective view showing the position of a third work zone relative to the digital radiography system according to another embodiment.

FIG. 11 shows a third work zone 303, shown in dotted line, having an operator console 311 that uses controls 292 positioned at another location on system 100. Controls 290 and 292 act as alternate operator interfaces, that is, as additional entry points for entering operator instructions that control setup of digital radiography system 100. In the example of FIGS. 10 and 11, second and third work zones 302, 303 both use second display 280.

The position of each work zone (e.g., 300, 302, 303) is based on considerations of x-ray imaging detector 160 placement relative to the patient and takes into account where the operator is favorably positioned for the different types of image that can be obtained. For digital radiography system 100, first, second, and third work zones (300, 302, 303) are separated from each other by a distance, typically by at least 1 meter or more. For example, in one embodiment, first and second work zones (300, 302) can be separated from each other by more than 2 meters.

Figure 12:
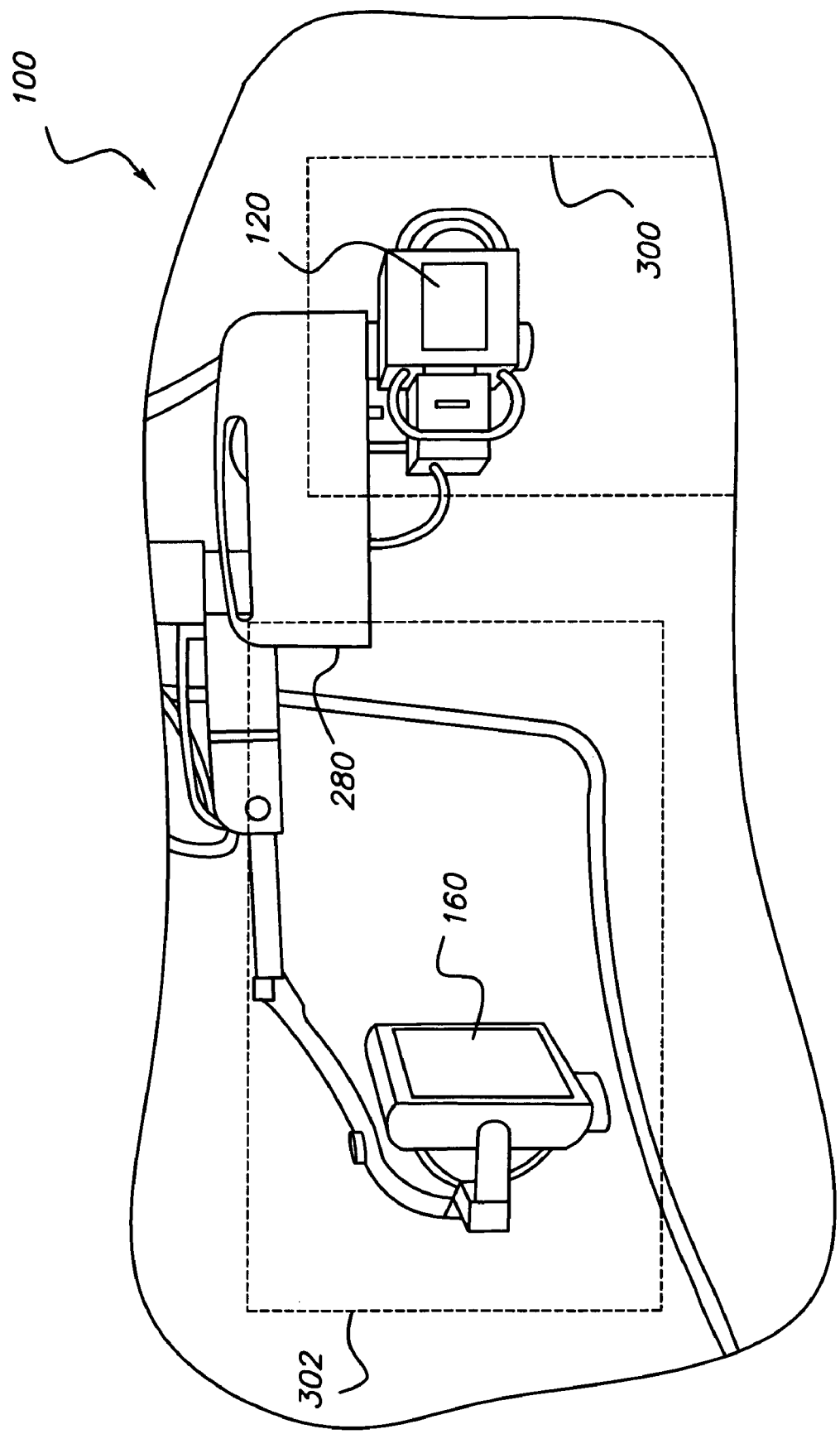
FIG. 12 shows a side view showing the relative positions of two separate work zones while in the horizontal operating position.

FIG. 12 shows relative positions of first and second work zones 300, 302 relative to digital radiography system 100 from one side of the equipment.

Figure 14:
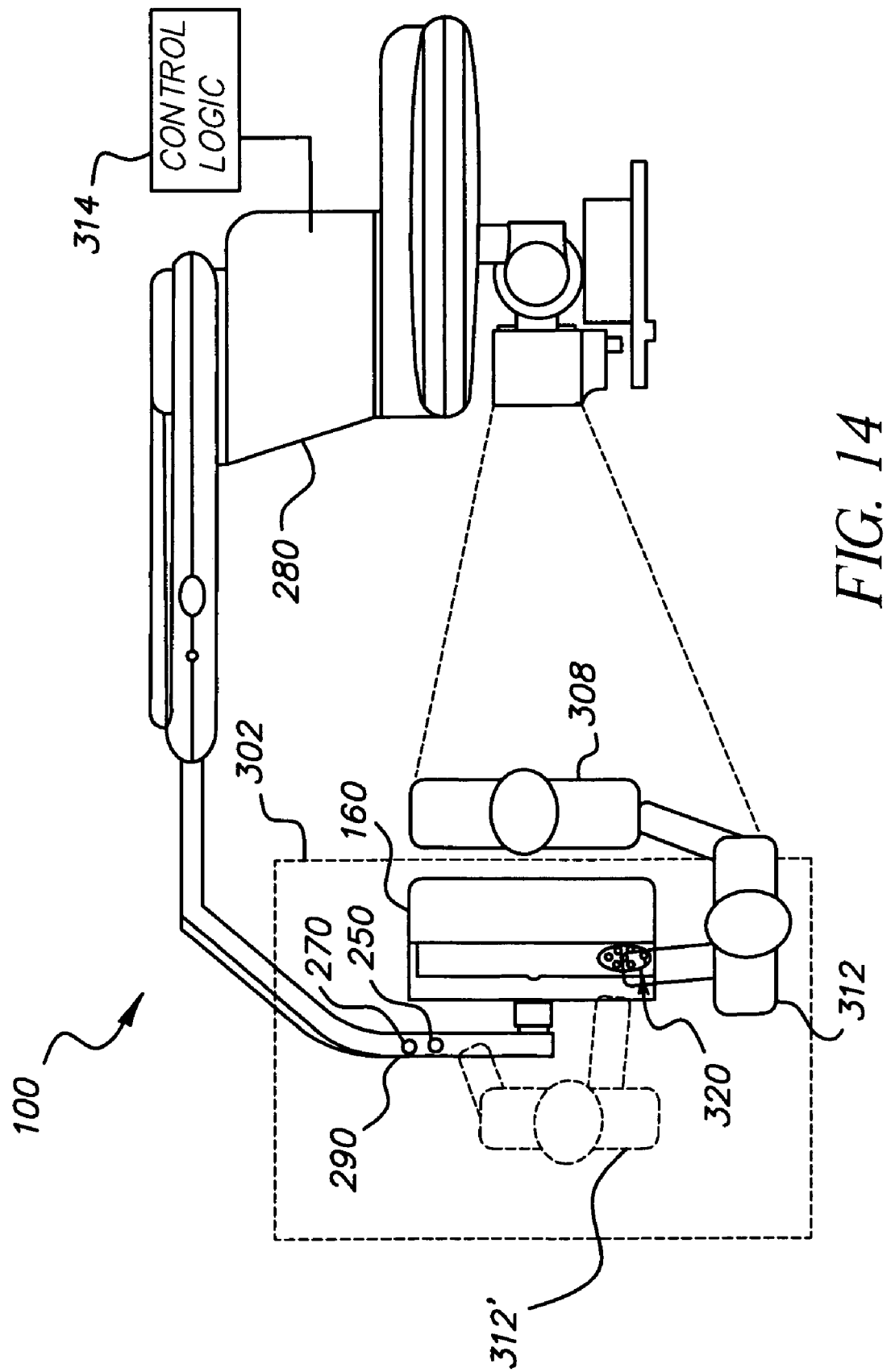
FIG. 14 shows a top view showing the position of a second work zone.
Figure 15:
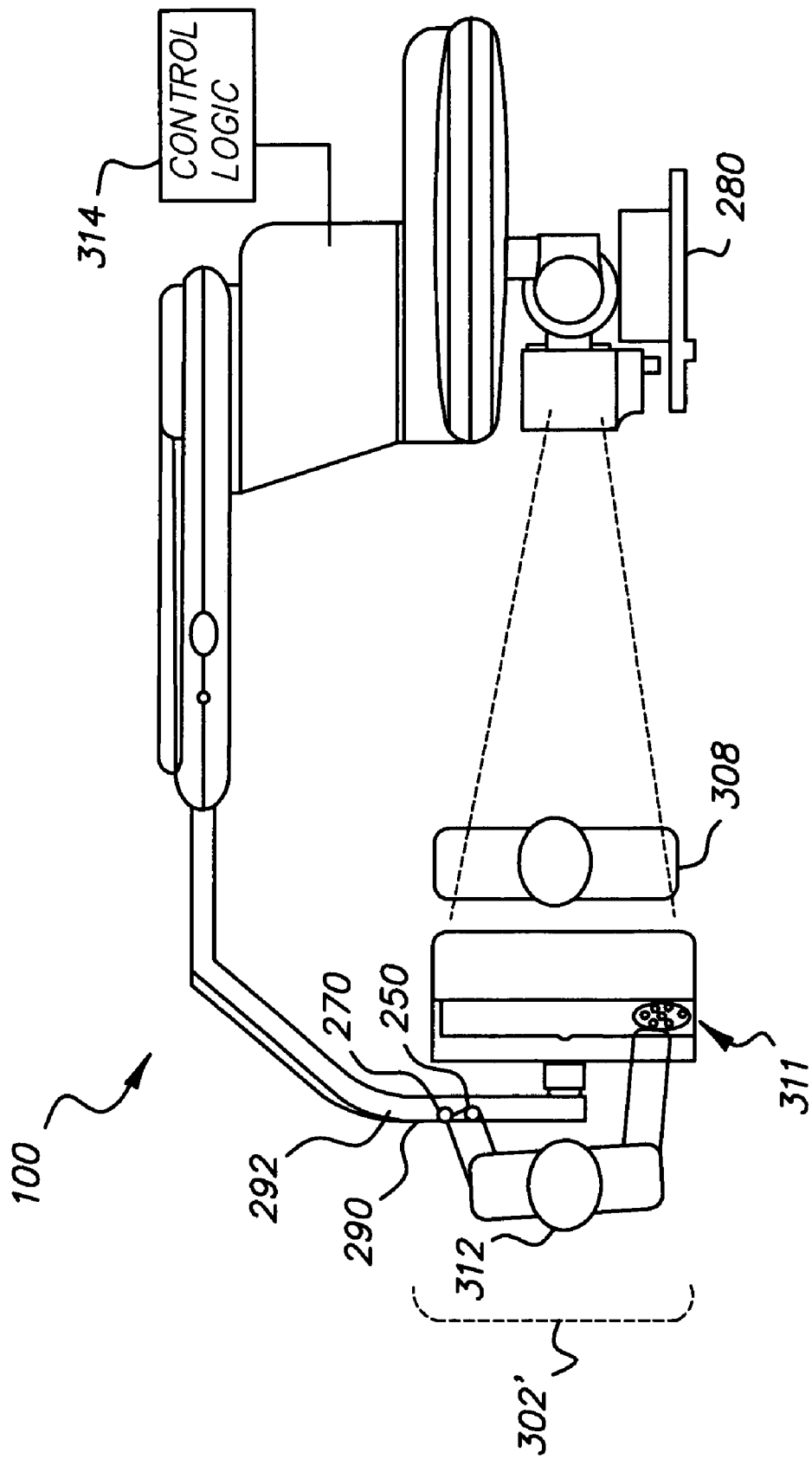
FIG. 15 shows a top view showing an alternate position of the second work zone.

FIGS. 13, 14, and 15 show, from a top view, component and working-space arrangements for first work zone 300 and second work zone 302. As shown in these figures, redundancy of controls and display functions give operator 312 flexibility, with the capability for maneuvering DR system 100 into position for patient 308 in a number of positions. For example, as shown in FIG. 14, operator 312 can set up imaging for patient 308 when working from the side of patient 308 or from a standing position just behind patient 308, as indicated in dashed outline at 312'. In second work zone 302, operator 312 or 312' has clear visibility of second display 280 and ease of access to second controls 290 of operator console 320. In third work zone 303 of FIG. 11, a separate set of operator controls 292 is positioned for easiest access and visibility from another operator position.

For controlling component placement from each work zone, a control logic processor 314, shown in FIGS. 13, 14, and 15, responds to operator commands and provides the control of content at displays 120 and 280. Control logic processor 314 can be a programmed logic control devices known to those skilled in the art, including for example, computer workstations or dedicated microprocessors.

Controls provided in work zones 301 and 302 are designed so that as digital radiography system 100 rotates in axis A (FIG. 4), controls of the alternate work zone rotate into the operator's view and within reach. That is, as operator 312' in FIG. 14 pushes the A axis break release 270 and pushes down on the support arm of detector 160, the controls of work zone 302 rotate downward as controls of work zone 303 rotate down into reach. Second display 280 will have remained stationary during this movement, keeping displayed information in view for operator 312' during this equipment re-positioning. Conversely controls of the second work zone 302 will rotate into the reach of operator 312' when the reverse rotation on the A axis is performed.

Figure 16:
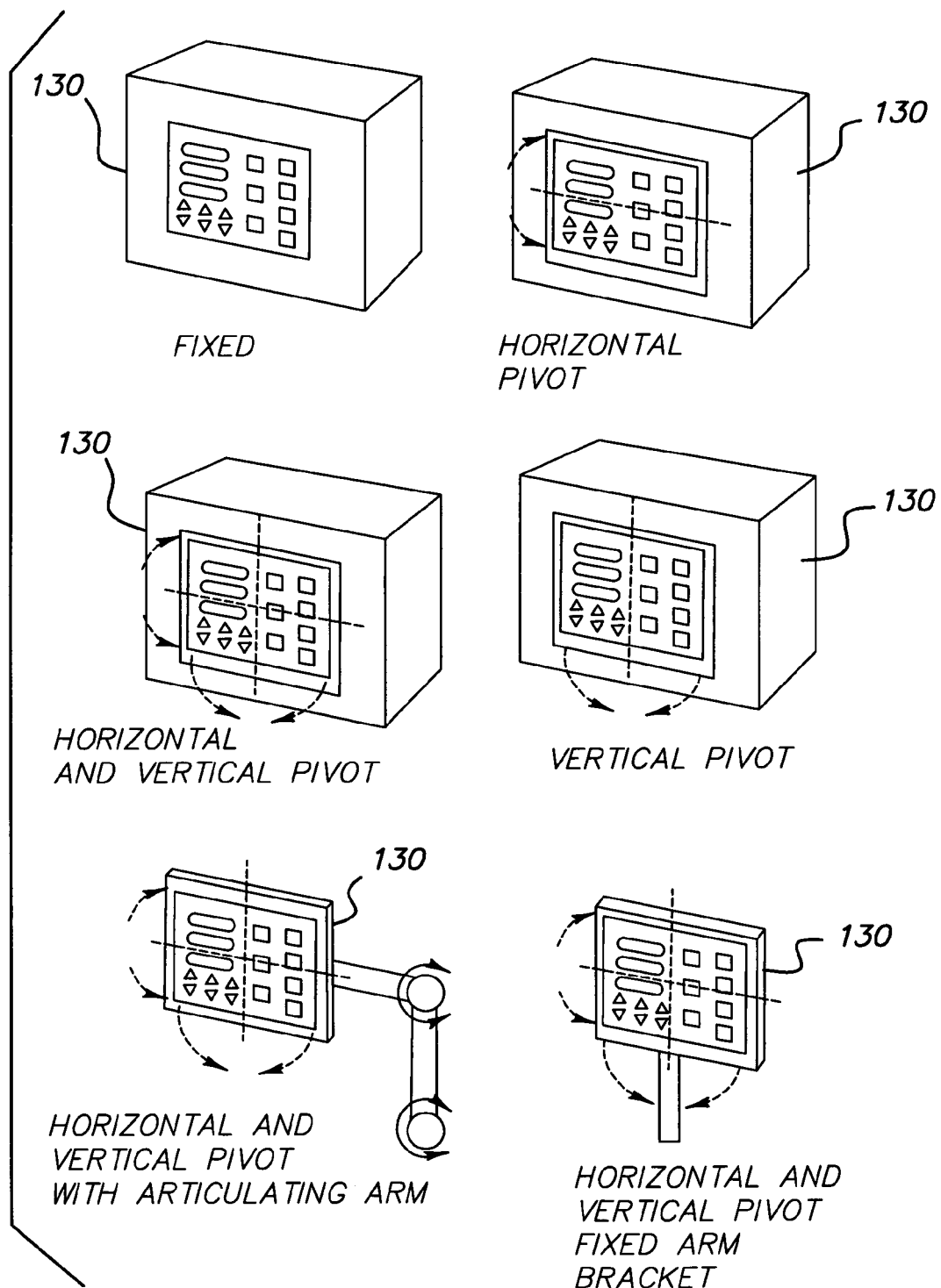
FIG. 16 shows a perspective view showing pivot positions for an operator control interface in one embodiment.

In addition to providing multiple work zones 300, 302, 303 the system of the present invention can enhance the ergonomics of the imaging process by allowing adjustment of control and display components to suit operator 312 when positioned at any of work zones 300, 302, or 303. Referring to FIG. 16, for example, operator control interface 130 can be pivoted with respect to both vertical and horizontal directions. In another embodiment, second controls 290 can be pivoted to at least some degree, alleviating strain on the operator and allowing a more natural system setup and operation for diagnostic imaging. Displays 120 and 280 can also be tilted in the X and Y axes to suit the viewing position of the operator.

In operation, DR system 100 can automatically respond to operator commands for system positioning, whether these commands are entered from operator control interface 130 in first work zone 300, from second controls 290 in second work zone 302, or from third work zone 303. Control logic at control logic processor 314 handles contention between commands entered at either of at least two work zones 300, 302 and determines what information appears at displays 120 and 280.

In one embodiment, displays 120 and 280 have identical content. Control functions can include XYZ positioning of x-ray source 110 and x-ray imaging detector 160; A, B, and SID manual brake releases; collimator controls; and z-axis, detector tilt, and SID motor controls. At least some of the operator commands, that is, a non-empty subset of the full set of available operator commands, can be entered at each work zone 300, 302, 303.

In one embodiment, the full set of operator commands is the subset that is available from operator control interface 130, second controls 290, and third controls 292.

In an alternate embodiment, one or more specific commands is disabled from one or more work zones 300, 302, 303, such as where it is not advisable for the operator, when operating within a specific work zone, to make mechanical adjustments of one or more components. This might be beneficial, for example, where visibility of a controlled component is obstructed from a certain operator position, relative to the support structure of the overall system.

Figure 17:
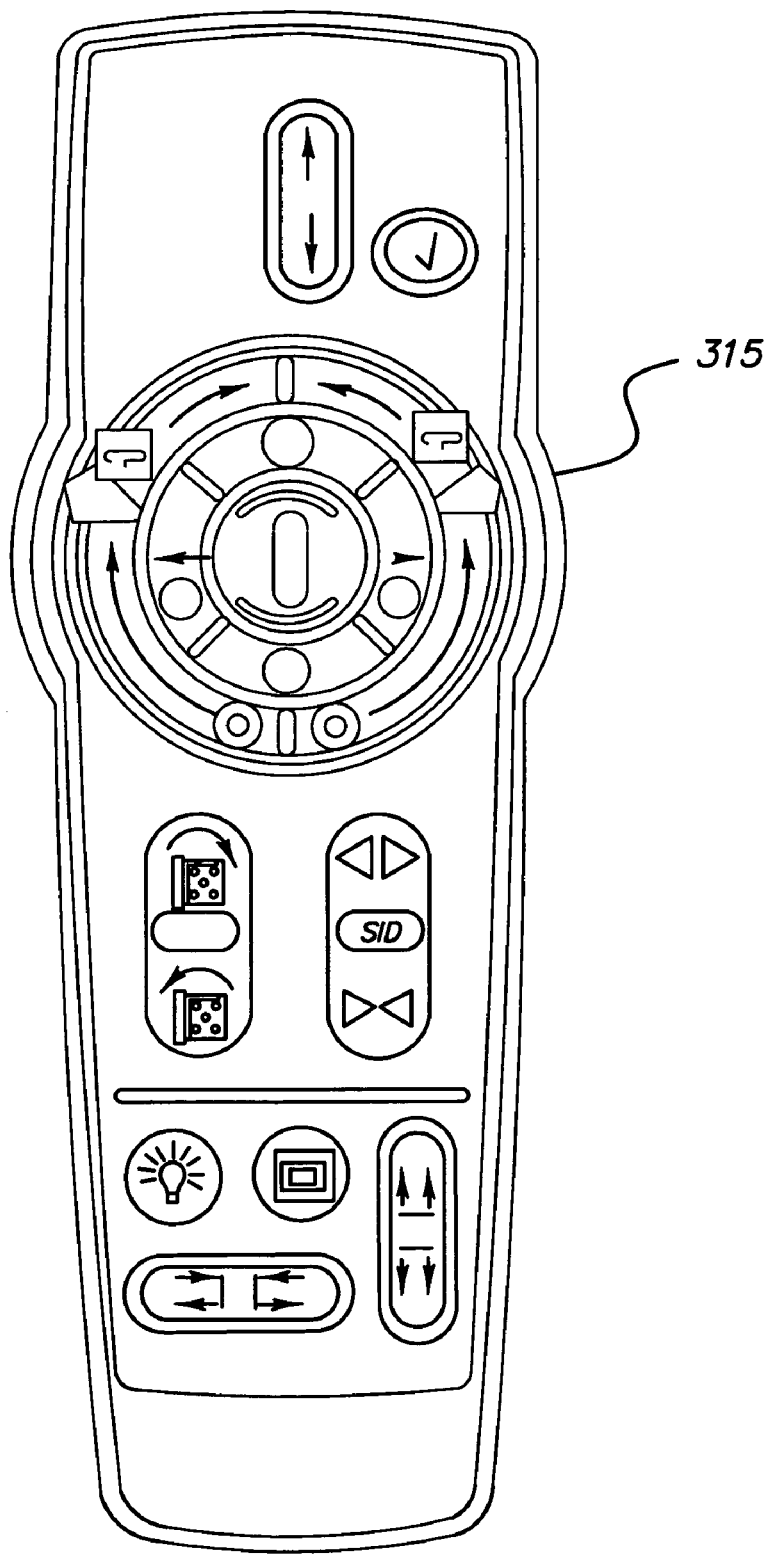
FIG. 17 shows a plan view showing a remote control used in one embodiment.
Figure 18:
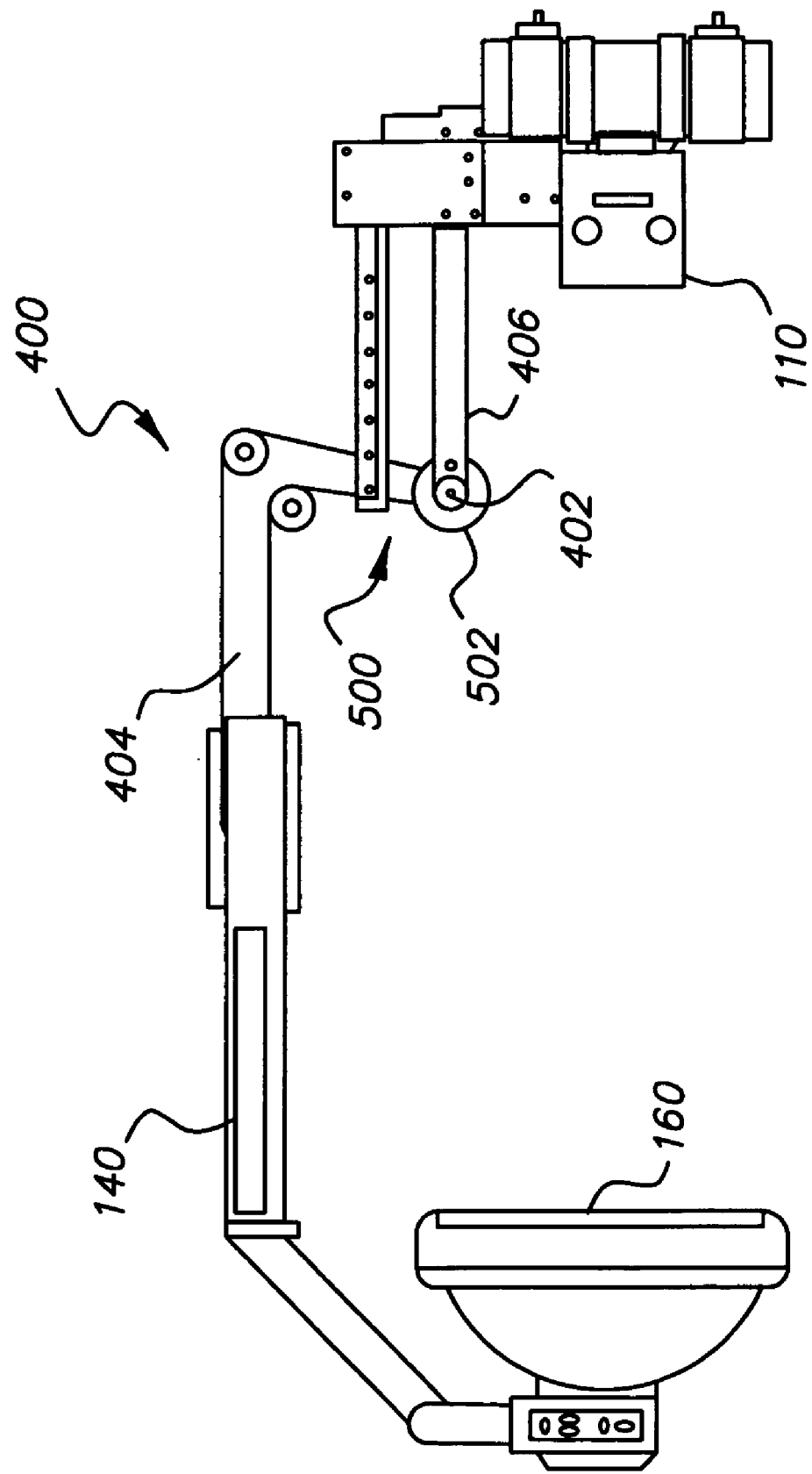
FIG. 18 shows a diagrammatic side view of the structure support, X-ray source, and X-ray imaging detector.
Figure 19:
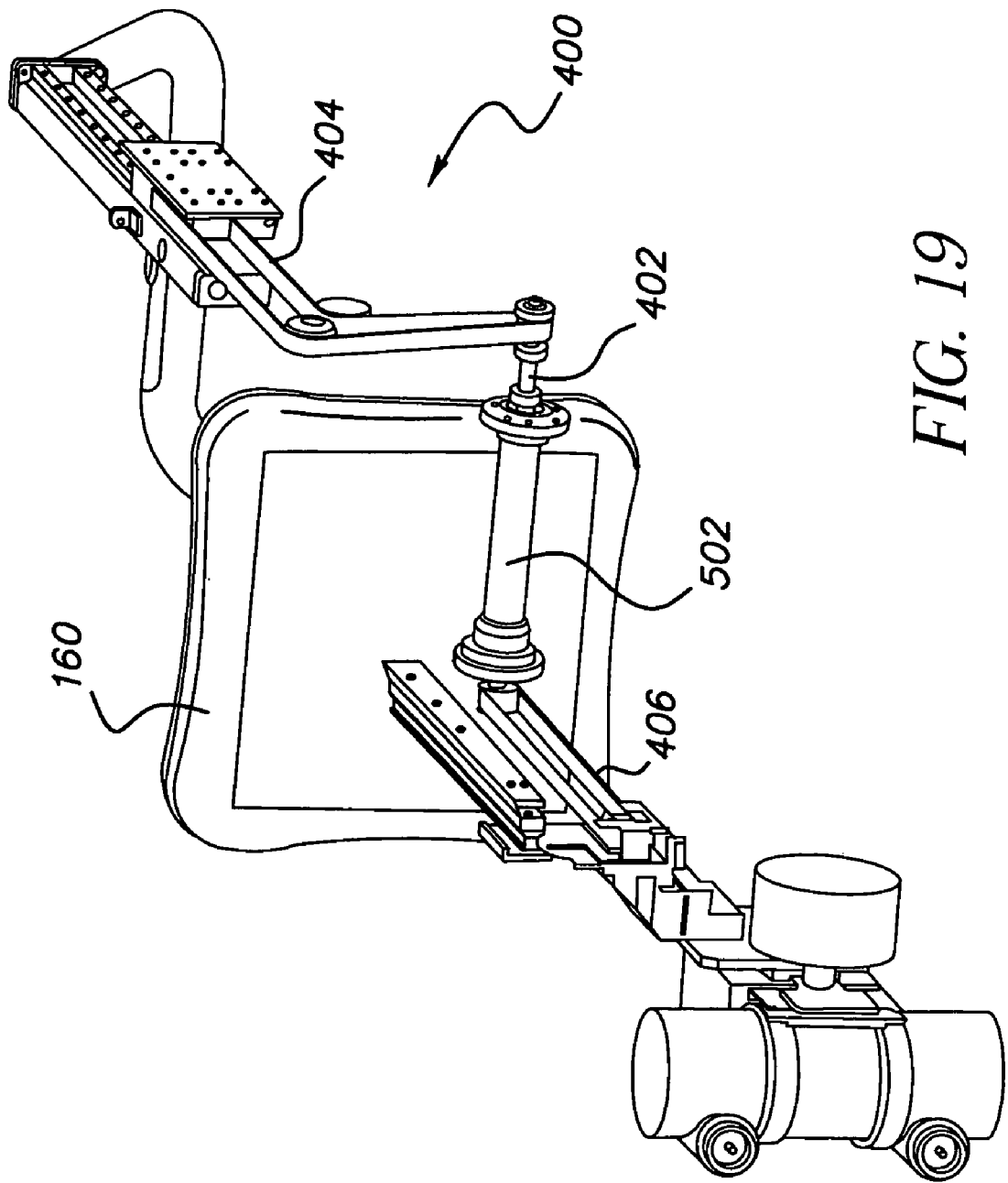
FIG. 19 shows a diagrammatic perspective view of FIG. 18.
Figure 20:
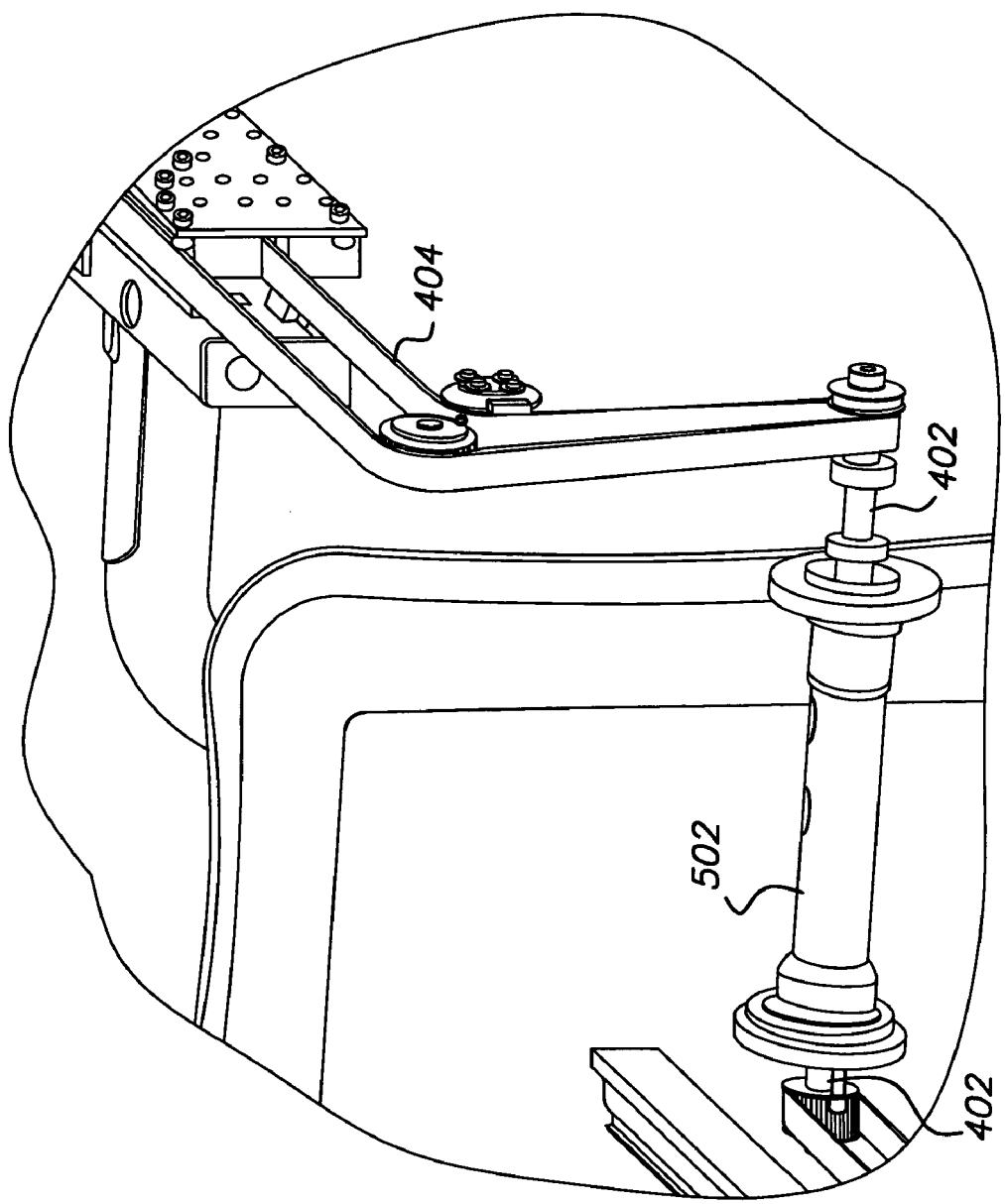
FIG. 20 shows an enlargement of a portion of FIG. 19.
Figure 21:
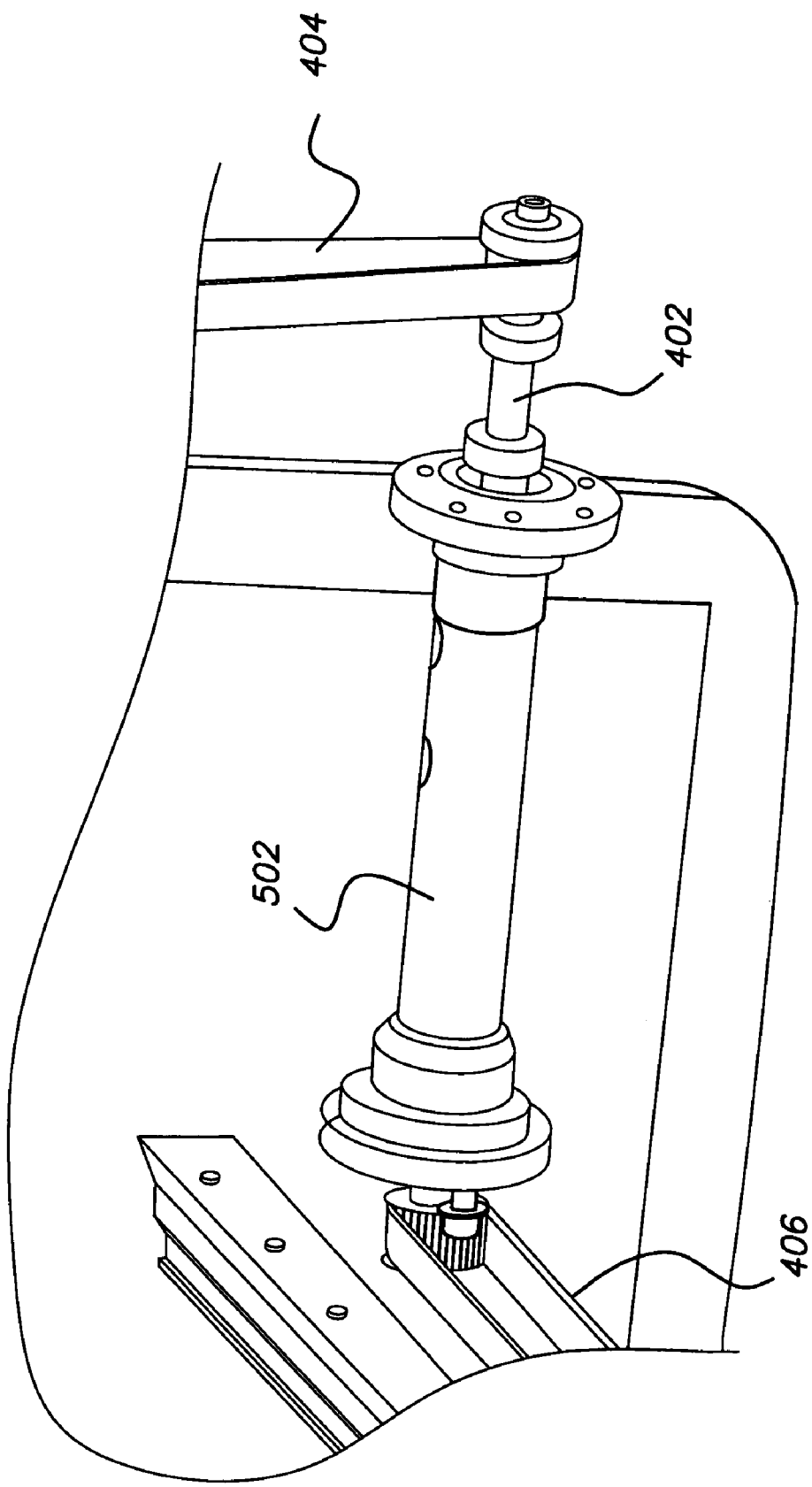
FIG. 21 shows an enlargement of a portion of FIG. 19.
Figure 22:
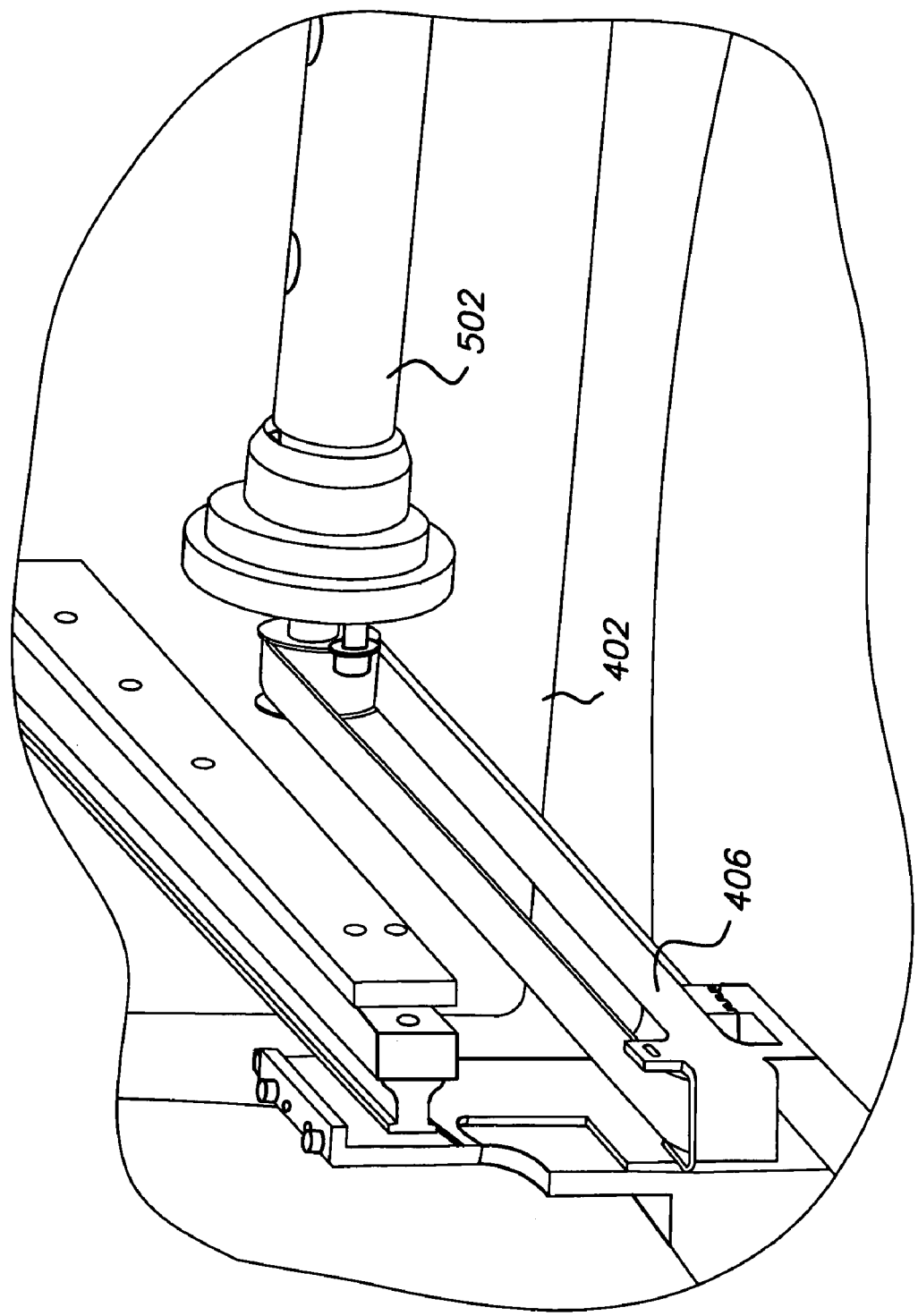
FIG. 22 shows an enlargement of a portion of FIG. 19.

Referring to FIG. 17, DR system 100 is operable by means of a hand-held device or remote control device 315 in one embodiment. For such an embodiment, remote control device 315 effectively creates a work zone whose boundaries depend on the operator's position. Within this variable work zone, remote control device 315 provides an operator console that includes operator control interface functions and may also provide display functions; alternately, another display (that is, a display that is not on remote control device 315) may be used when remote control device 315 serves for command entry.

Remote control device 315 can communicate with control logic processor 314 (FIGS. 13-15) using tethered wire connection, wireless connection, network connection, or other signal communication means. Remote control device 315 can be used from any operator position; however, there may be a different set of commands available remotely from those available with the operator in work zones 300, 302, 303. The wireless hand-held embodiment of this operator control interface is particularly advantaged where an operator may require close proximity to the patient during setup.

Display content that appears on displays 120 and 280 can include, for example, data on SID distance, patient identification, operator identification, and information on what series of images are required for a particular patient. In another embodiment, one or both of displays 120 and 280 can show different information. For example, display 120, not easily visible to patient 308, can show smaller scale images or thumbnails that guide the operator in positioning x-ray source 110 and detector 160.

For the operator, useful display content can include:
(i) Access to patient records for the current patient;
(ii) Access to patient schedule and to other schedule needs, particularly where there may be patients in line for imaging at this same apparatus;
(iii) Access to instructions about device controls;
(iv) Information on power settings and device positioning data;
(v) Equipment and display status data, including operability, locked/unlocked status;
(vi) Instructions for obtaining images, including general instructions for operation and specific instructions from attending physician;
(vii) Information related to images needed;
(viii) Equipment status, service procedures, and preventive maintenance data.

The display content can include text, video, and animations where appropriate. Speakers (not shown) may be provided for audible information and prompting.

In one embodiment, second display 280 does not duplicate the information that is displayed at first display 120, but can be changed to show other types of information or images to be viewed by patient 308. Educational information or instructions for the patient can be displayed on the monitor. For example, display 280 may show a presentation on how an exam is to be conducted, with instructions to the patient about movement, breathing, relaxation, or maintaining a position. An animated presentation may describe how the image is obtained or describe the purpose of the data.

In another embodiment, display 280 can be used to display moving or still images that are related to expressed interests of the patient. For example, thematic selections may include scenes with animals, sports events, nature landscapes, people, or other themes. These can be particularly helpful for relaxing a patient and providing a means to focus patient attention, aiding in stress reduction. During apparatus configuration, the operator can toggle between display of information and images intended for the patient and control setup information needed by the operator for the imaging session. Operator information can also display unobtrusively along one or more edges of the display screen, where the full display itself is largely directed to the patient.

Images displayed for the patient can be selected according to a patient preference. Images can alternately be selected at random. Images can include still images, animated images, or video images, for example. Audio content related to the images can also be provided. Images can display at any suitable time, including before, during, and after image capture.

As noted earlier, redundancy of controls or display has not been a feature of radiological systems for medical imaging. Instead, existing apparatus have required continual back-and-forth movement of the operator between a control console and the patient during equipment setup. The arrangement of the present invention, by providing multiple, suitably positioned work zones for imaging personnel, utilizes control console redundancy to improve work flow and to best suit the needs of both the patient and the operator of the diagnostic imaging equipment. As part of this feature, display redundancy allows the operator to observe key setup parameters when necessary and also permits the display of content suited to the patient.

The present invention provides improved flexibility and usability of complex radiographic equipment by adapting some of the principles of redundant display and control to the imaging workflow. The present operation facilitates the operation of a complex radiological system that is designed to obtain patient images where the patient can be in any number of positions, from vertical to horizontal. Using the apparatus and methods of the present invention, an operator can flexibly work from an advantageous position when setting up the imaging equipment for the patient. The need for operator movement around the equipment is minimized, improving the overall system ergonomics and making system operation more efficient.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, more than two or three work zones can be used, as shown in FIGS. 9-11. As noted earlier, the set of control functions and capabilities at different work zones can be the same or can be varied, providing a partial subset of control functions that best suit operator convenience. While digital X-ray radiography system 100 has been described in detail for one embodiment, the approach used in the present invention can be applied to other diagnostic imaging apparatus that allow flexibility of placement for the radiation source and sensing apparatus. For example, imaging detector 160 could alternately be a cassette containing any type of photosensitive medium, including film or photostimulable phosphor, for example.

Support structure 140 is now more particularly described.

Digital radiography system 100 includes X-ray source 110, first display 120, operator control interface 130, support structure 140, and X-ray imaging detector 160 with coupling 170. X-ray source 110 is connected to support structure 140 by coupling 112 (FIGS. 6-7) that allows X-ray source 110 to rotate in the C and C' directions (FIG. 4). If desired, coupling 170 can be employed to permit X-ray imaging detector 160 to move in the D and D' directions (FIG. 4), and to rotate so as to orient X-ray imaging detector 160 into a portrait or landscape position. Support structure 140 is pivotally mounted for rotation about an axis 145 (FIGS. 4 and 6) to obtain the A and A' rotation.

Support structure 140 include a support arm 141 which is linearly adjustable (e.g., in the E and E' directions of FIG. 7) so as to allow an operator to set the source-to-image (SID) distance between X-ray source 110 and X-ray imaging detector 160. X-ray source 110 is linearly moveable in directions F and F' (FIG. 7) along support structure 140 so as to adjust the source-to-image distance before capturing an image of a subject (FIGS. 4-6).

Support structure 140 is rotatable about an axis 145 in the A and A' directions (FIG. 4) by an operator in preparation for capturing an image of subject 195.

As illustrated in FIGS. 4-6, support structure 140 is connected to telescoping support member 180 by coupling 155 (FIG. 6). Telescoping support member 180 is adjustable in the Z and Z' directions (FIGS. 4 and 5) to varying positions between a collapsed position and an extended position.

Support structure 140 allows digital radiography system 100 to image a variety of subjects (e.g., subject 195 illustrated in FIGS. 4-6), which can be an individual or a body part of the individual), whether the subject is standing (e.g., see subject 195 of FIG. 4), reclining on a table (e.g., see subject 195 of FIGS. 5 and 6), or sitting. Support structure 140 is configured to slide inward and outward in overlapping sections in directions E and E' (FIG. 7), so as to move the location of X-ray imaging detector 160. X-ray source 110 is moveable linearly to discreet positions in the F and F' directions (FIG. 7) along support structure 140 to provide further adjustment of digital radiography system 100 for imaging. As will be described in more detail below, through a mechanical connection, X-ray source 110 and X-ray imaging detector 160 simultaneously move the same linear distance, but in opposing directions. The positioning of X-ray source 110 and X-ray imaging detector 160 by an operator can achieve an appropriate source-to-image distance for imaging of the subject to occur. As indicated in FIG. 4, the source-to-image distance is the linear distance between X-ray source 110 and X-ray imaging detector 160.

B-direction control 240 allows an operator or technician to control the rotational motion of support structure 140 in a plane parallel to the ground (e.g., movement in the B and B' directions illustrated in FIG. 4 and as illustrated in FIGS. 2 and 4).

Figure 7:
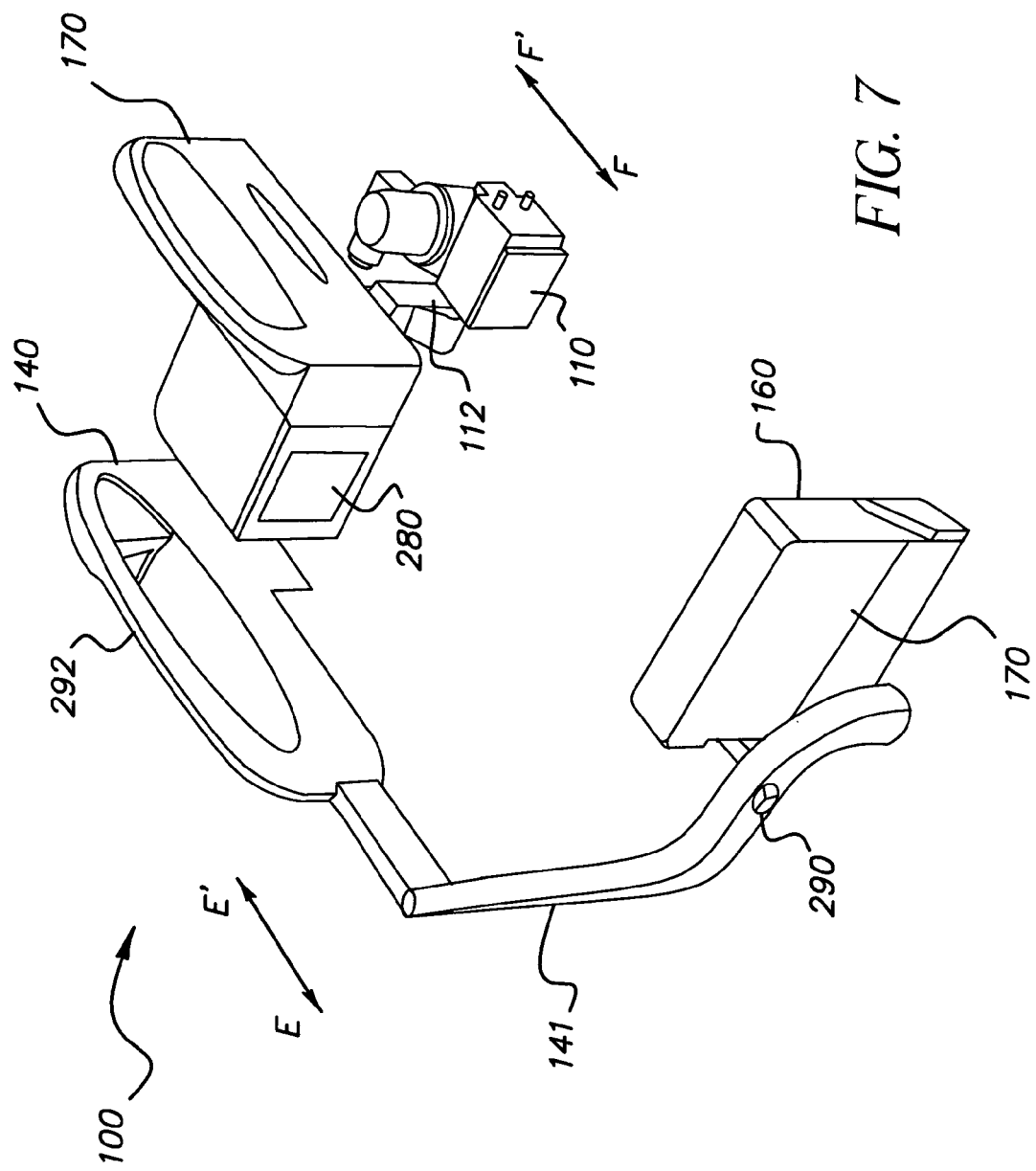
FIG. 7 shows another diagrammatic view of the support structure, X-ray source and X-ray imaging detector of the digital radiography system of FIG. 1.

Source-to-image distance release control 250 can control movement of support structure 140 (for movement of X-ray imaging detector 160 in the E and E' directions indicated in FIG. 7). Using source-to-image distance release control 250, an operator can also move X-ray source 110 in the F and F' directions (FIG. 7) on support structure 140 so as to change the source-to-image distance (FIG. 4) between X-ray source 110 and X-ray imaging detector 160. X-ray source tilt control 260 allows an operator or technician to adjust the angular movement of X-ray source 110 in the C and C' directions (FIG. 4).

Referring now to FIGS. 18-22, support structure 140 includes a translational assembly 400 that enables X-ray source 110 and X-ray imaging detector 160 to simultaneously move the same linear distance/amount, but in opposing directions (directions E and E' and F and F' of FIG. 7). Through the mechanical connection, X-ray source 160 cannot translate independently of x-ray detector 110.

Translational assembly 400 includes a drive shaft 402, a first drive member 404, and a second drive member 406. First drive member 404 is shown in FIGS. 18-22 as a belt connecting one end of drive shaft 402 and X-ray imaging detector 160. Second drive member 406 is shown in FIGS. 18-22 as a belt connecting the other end of drive shaft 402 and X-ray source 110. As such, drive shaft 402 provides a mechanical connection between the X-ray source and X-ray detector. That is, the translation of the X-ray source and X-ray detector is connected through a drive shaft. Note that the two drive members are not physically aligned nor have a direct linear connection. The X-ray source and X-ray detector do not employ the same linear translation member.

Support structure 140 further includes a rotational assembly 500 that enables rotation of X-ray source 110 and X-ray imaging detector 160 as described above and shown in FIG. 2 about axis 145.

Still referring to FIGS. 18-22, rotational assembly 500 includes a rotational shaft 502. Rotational shaft 502 is concentric with drive shaft 402, but drive shaft 402 and rotational shaft 502 are not connected (except through bearings). Rather, drive shaft 402 is disposed through and rotates within rotational shaft 502.

Figure 23:
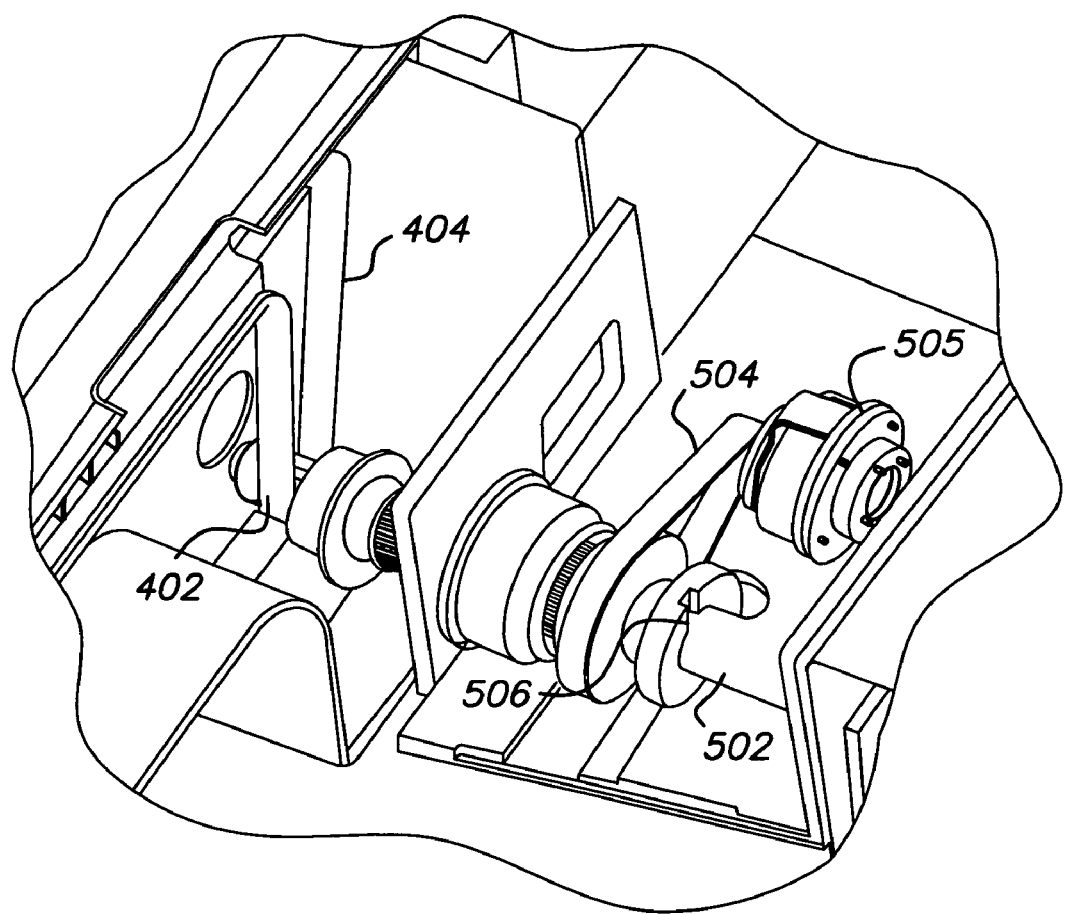
FIG. 23 shows a diagrammatic perspective view of portions of the rotational assembly and translational assembly.

As shown in FIG. 23, drive means 504 (shown as a belt/chain) is used to rotate rotational shaft 502. As shown in FIG. 23, drive means 504 is driven by a motor (not shown) through a clutch 505. It is noted that rotational shaft 502 can be manually operated.

Detents are described above to control the rotation of the system. Detents 506 on rotational shaft 502 can be employed to position the shaft/apparatus into predetermined locations.

Thus, what is provided is an apparatus and method for digital radiography using multiple work zones for expanded access to imaging controls and display.

| PARTS LIST | |
|---|---|
| 100 | Digital radiography (DR) system |
| 110 | X-ray source |
| 112 | Coupling |
| 120 | First Display |
| 130 | Operator control interface |
| 140 | Support structure |
| 141 | Support arm |
| 145 | Axis |
| 147 | Axis |
| 150 | Coupling |
| 152 | Axis |
| 155 | Coupling |
| 160 | X-ray imaging detector |
| 170 | Coupling |
| 180 | Telescoping support member |
| 190 | Moveable base |
| 195 | Subject |
| 210 | X-direction control |
| 220 | Y-direction control |
| 230 | Z-direction control |
| 240 | B-direction control |
| 245 | Detent skip control |
| 250 | SID release control |
| 260 | X-ray source tilt control |
| 270 | A-direction control |
| 280 | Second display |
| 290 | Controls |
| 292 | Third controls |
| 300, 302, 302', 303. | Work zone |
| 308 | Patient |
| 310 | Operator console |
| 311 | Operator console |
| 312, 312' | Operator |
| 314 | Control logic processor |
| 315 | Remote control |
| 320 | Operator console |

The invention claimed is:

1. A radiography apparatus comprising:
   an x-ray source;
   an x-ray imaging detector;
   a support structure coupled to the x-ray source and to the x-ray detector and rotatable about first and second orthogonal axes and linearly moveable, the x-ray source and the x-ray imaging detector each being independently rotatable about third and fourth axes, respectively, to thereby provide an operator with a number of degrees of freedom of motion of the x-ray source and the x-ray imaging detector to move them to different positions relative to a subject;
   a first operator control console including a first command entry device for entry of operator setup instructions and a first display;
   a second operator control console spaced from the first operator control console and comprising a second command entry device for entry of operator setup instructions and a second display; and
   a control logic processor responsive to operator setup instructions for controlling operation of the radiography apparatus, wherein at least some of the operator setup instructions entered at the first command entry device and operator setup instructions entered at the second command entry device are the same;

wherein the support structure includes a translational assembly and a rotational assembly, the translational assembly adapted to affect simultaneous linear movement of the x-ray source and to the x-ray detector in opposing directions, the rotational assembly adapted to affect rotation of the x-ray source and the x-ray detector about the first and second orthogonal axes, wherein the translational assembly includes:

a first drive member affecting translation of the x-ray source;

a second drive member, spaced from the first drive member, affecting translation of the x-ray detector; and a drive shaft connecting the first and second drive members.

2. The radiography apparatus of claim 1, further comprising a third operator control console spaced from the first and second operator consoles and comprising a third command entry device for entry of operator setup instructions.

3. The radiography apparatus of claim 1, wherein the imaging detector comprises a digital detector, a photostimulable phosphor medium, or a photosensitive film medium.

4. The radiography apparatus of claim 1, wherein the translational assembly and rotational assembly are concentric.

* * * * *

UNITED STATES PATENT AND TRADEMARK OFFICE
CERTIFICATE OF CORRECTION

PATENT NO. : 7,481,578 B2  Page 1 of 1
APPLICATION NO. : 11/532573
DATED : January 27, 2009
INVENTOR(S) : Chapman It is certified that error appears in the above-identified patent and that said Letters Patent is hereby corrected as shown below:

Title page, item (73) Assignee: Should read -- Carestream Health, Inc., Rochester, NY (US) --

Signed and Sealed this

Twenty-seventh Day of April, 2010

David J. Kappos
*Director of the United States Patent and Trademark Office*